United States Patent
Davila

(10) Patent No.: US 12,065,474 B2
(45) Date of Patent: *Aug. 20, 2024

(54) CHIMERIC ANTIGEN RECEPTORS WITH MUTATED CD28 COSTIMULATORY DOMAINS

(71) Applicant: H. Lee Moffitt Cancer Center and Research Institute, Inc., Tampa, FL (US)

(72) Inventor: Marco L. Davila, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 1060 days.

This patent is subject to a terminal disclaimer.

(21) Appl. No.: 16/629,046

(22) PCT Filed: Jul. 6, 2018

(86) PCT No.: PCT/US2018/041040
§ 371 (c)(1),
(2) Date: Jan. 7, 2020

(87) PCT Pub. No.: WO2019/010383
PCT Pub. Date: Jan. 10, 2019

(65) Prior Publication Data
US 2020/0129554 A1    Apr. 30, 2020

Related U.S. Application Data

(60) Provisional application No. 62/529,919, filed on Jul. 7, 2017.

(51) Int. Cl.
*A61K 35/17* (2015.01)
*A61K 39/00* (2006.01)
(Continued)

(52) U.S. Cl.
CPC ... *C07K 14/7051* (2013.01); *A61K 39/001111* (2018.08); *A61P 35/02* (2018.01);
(Continued)

(58) Field of Classification Search
None
See application file for complete search history.

(56) References Cited

U.S. PATENT DOCUMENTS

2015/0140023 A1   5/2015   Birkle et al.
2016/0046712 A1   2/2016   Brogdon et al.
(Continued)

FOREIGN PATENT DOCUMENTS

EA    027153 B1    3/2017
WO    2018140725 A1    8/2018
WO    WO-2018140725 A1 *    8/2018 ............. A61K 35/17

OTHER PUBLICATIONS

Pagan et al., J Immunol Sep. 15, 2012; 189(6): 2909-2917 (Year: 2012).*

(Continued)

*Primary Examiner* — Karl J Puttlitz
(74) *Attorney, Agent, or Firm* — Thomas | Horstemeyer, LLP

(57) ABSTRACT

Disclosed herein are chimeric antigen receptor (CAR) polypeptides, which can be used with adoptive cell transfer to target and kill cancers, that comprise a co-stimulatory signaling region having a mutated form of a cytoplasmic domain of CD28 that enhances CAR-T cell function, e.g. by reducing CAR-T cell exhaustion. Also disclosed are immune effector cells, such as T cells or Natural Killer (NK) cells, that are engineered to express these CARs. Therefore, also disclosed are methods of providing an anti-tumor immunity in a subject with a tumor associated antigen-expressing cancer that involves adoptive transfer of the disclosed (Continued)

immune effector cells engineered to express the disclosed CARs.

10 Claims, 23 Drawing Sheets

Specification includes a Sequence Listing.

(51) Int. Cl.
    *A61P 35/02*     (2006.01)
    *C07K 14/705*     (2006.01)
    *C07K 14/725*     (2006.01)
    *C07K 16/28*     (2006.01)
    *C12N 15/62*     (2006.01)

(52) U.S. Cl.
    CPC .... *C07K 14/70521* (2013.01); *C07K 16/2803* (2013.01); *C07K 16/2809* (2013.01); *C07K 16/2818* (2013.01); *C12N 15/62* (2013.01); *C07K 2319/33* (2013.01); *C12N 2510/00* (2013.01)

(56) References Cited

U.S. PATENT DOCUMENTS

| | | | | |
|---|---|---|---|---|
| 2016/0046724 | A1* | 2/2016 | Brogdon | C07K 19/00 435/328 |
| 2020/0216534 | A1* | 7/2020 | Davila | C07K 14/70521 |
| 2021/0371540 | A1* | 12/2021 | Abate-Daga | C07K 14/70521 |
| 2023/0265184 | A1* | 8/2023 | Davila | C07K 14/70521 |

OTHER PUBLICATIONS https://en.wikipedia.org/wiki/CAR_T_cell visited Aug. 14, 2023. (Year: 2023).*

Long, Adrienne H., et al., "4-1BB costimulation ameliorates T cell exhaustion induced by tonic signaling of chimeric antigen receptors," Nature Medicine, vol. 21, No. 6 (2015) (28 pages).

Thods, Supplementary Text and Figures (2015), pp. 13, 153.

Office Action, Japan Patent App. 2019-571984, issued Jan. 18, 2022.

International Search Report issued by the European Patent Office for application 18828264.4, mailed May 4, 2021.

Davila et al., CD19 CAR-Targeted T Cells Induce Long-Term Remission and B Cell Aplasia in an Immunocompetent Mouse Model of B Cell Acute Lymphoblastic Leukemia, PLoS One, vol. 8, No. 4, 1-14, 2013.

Hong et al., LI Cell Adhesion Molecule-Specific Chimeric Antigen Receptor-Redirected Human T Cells Exhibit Specific and Efficient Antitumor Activity against Human Ovarian Cancer in Mice, PLoS One, vol. 11, No. 1, 1-18, 2016.

Kofler et al., CD28 Costimulation Impairs the Efficacy of a Redireted T-cell Antitumor Attack in the Presence of Regulatory T cells Which Can Be Overcome by Preventing Lck Activation, Molecular Therapy, vol. 19, No. 4, 760-767, 2011.

Long et al., 4-IBB costimulation ameliorates T cell exhaustion induced by tonic signaling of chimeric antigen receptors, Nature Medicine, vol. 21, No. 6, 581-590, 2015.

Posey et al., Mixed Signals: Alteration of CD28 Signaling Motifs Improves Anti-Tumor Efficacy and Persistence of CAR T Cells, Molecular Therapy, vol. 5, No. S1, 154, 2017.

Abate-Dage et al., CAR models: next-generation CAR modifications for enhanced T-cell function. Mol Ther Oncolytics, vol. 3, p. 1-7, 2016.

Liu et al., A Chimeric Switch-Receptor Targeting PD1 Augments the Efficacy of Second-Generation CAR T Cells in Advanced Solid Tumors, Cancer Res., vol. 76(6), p. 1578-90, 2016.

Liu et al., Targeting the phosphoinositide 3-kinase (PI3K) pathway in cancer, Nat Rev Drug Discov., vol. 8(8), p. 627-44, 2009.

Pagan et al., CD28 Promotes CD4+ T Cell Clonal Expansion during Infection Independently of Its YMNM and PYAP Motifs., J Immunol., vol. 189(6), p. 2909-17, 2012.

Parry et al., Signalling to suit function: tailoring phosphoinositide 3-kinase during T-cell activation, Trends Immunol., vol. 28(4), p. 161-8, 2007.

International Search Report issued for application PCT/US20118/041040, mailed Sep. 19, 2018.

Search Report issued by the Singapore Patent Office issued for application 11201911838U, completed Jul. 23, 2021.

Boomer et al., An Enigmatic Tail of CD28 Signaling. Cold Spring Harb Perspect Biol, vol. 2, No. 8 (2010), pp. 1-20.

Office Action, Russia Patent Application 2020104792, issued Nov. 2, 2021.

* cited by examiner

|       | YMNM | PRRP | PYAP |
|-------|------|------|------|
| CD28  | YMNM | PRRP | PYAP |
| Mut01 | AAAA | PRRP | PYAP |
| Mut02 | YMNM | AAAA | PYAP |
| Mut03 | YMNM | PRRP | AAAA |
| Mut04 | YMNM | AAAA | AAAA |
| Mut05 | AAAA | PRRP | AAAA |
| Mut06 | AAAA | AAAA | PYAP |
| Mut07 | AAAA | AAAA | AAAA |

FIG. 2A

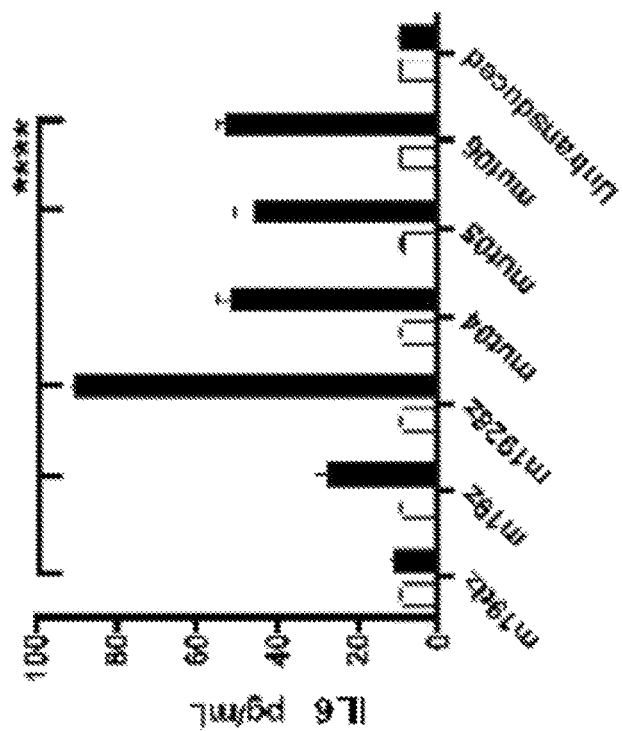
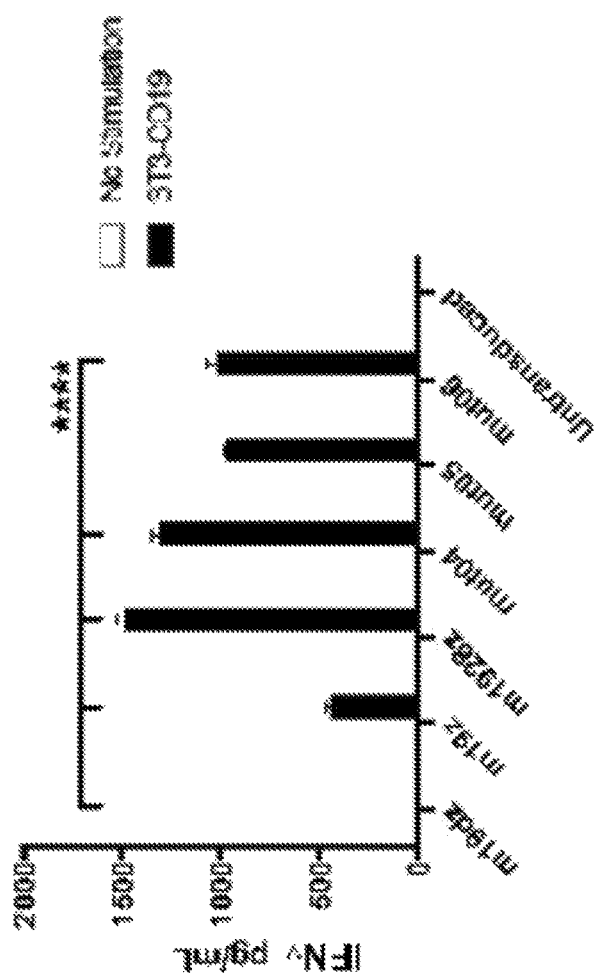
FIG. 6A
FIG. 6B

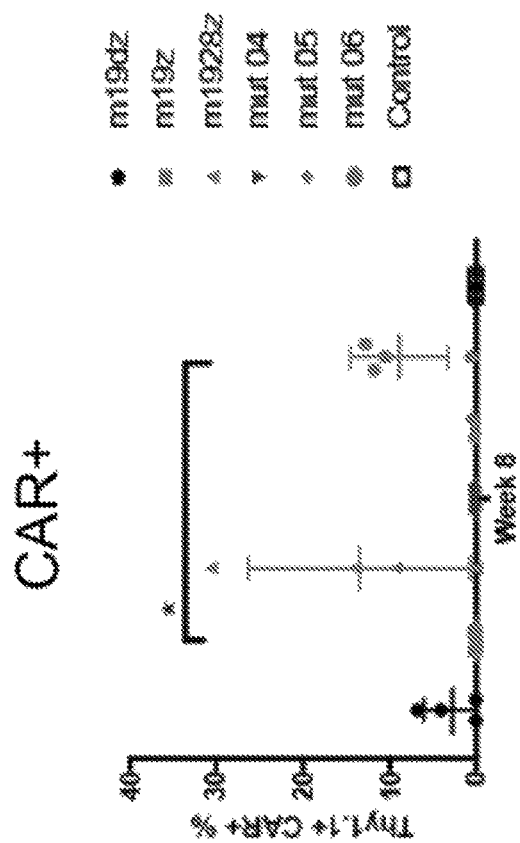
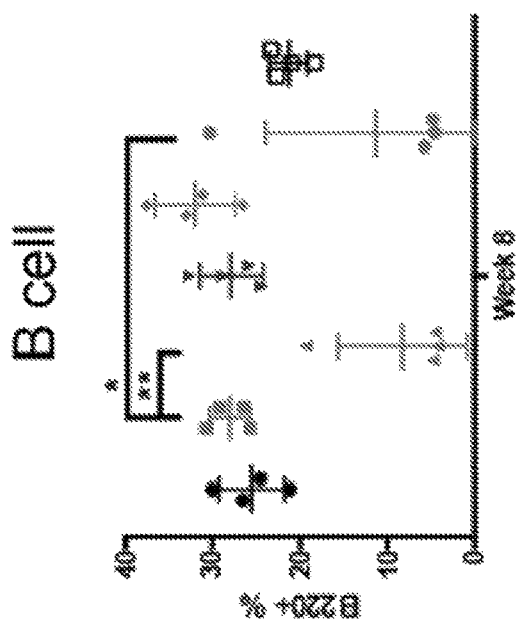
FIG. 9B
FIG. 9A

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct

<400> SEQUENCE: 1

Tyr Met Asn Met
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Pro Arg Arg Pro
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Pro Tyr Ala Pro
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct

<400> SEQUENCE: 4

Ala Ala Ala Ala
1
```

CHIMERIC ANTIGEN RECEPTORS WITH MUTATED CD28 COSTIMULATORY DOMAINS

CROSS-REFERENCE TO RELATED APPLICATIONS

This application claims benefit of U.S. Provisional Application No. 62/529,919, filed Jul. 7, 2017, which is hereby incorporated herein by reference in its entirety.

SEQUENCE LISTING

This application contains a sequence listing filed in electronic form as an ASCII.txt file entitled "320803_2160_Sequence_Listing_ST25" created on Jul. 7, 2018. The content of the sequence listing is incorporated herein in its entirety.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are properly harnessed.

A major advance for anti-cancer T cell therapy is the chimeric antigen receptor (CAR), which is a single chain variable fragment (scFv) derived from an antibody fused to the signaling domains of a T cell receptor (TCR) (Davila, M. L., et al., Oncoimmunology, 2012. 1(9):1577-1583). The intracellular domain of a first-generation CAR includes only CD3ζ, while second-generation CARs also include co-stimulatory domains such as CD28 or 41BB. These second-generation CAR domains support highly-efficacious tumor killing in mice and led to the clinical evaluation of CAR T cell therapies in patients. The potential of CD19-targeted CAR T cells was confirmed by reports of complete remission rates of 90% for patients with B cell acute lymphoblastic leukemia (B-ALL) (Davila, M. L., et al., Sci Transl Med, 2014. 6(224):224ra25; Maude, S. L., et al., N Engl J Med, 2014. 371(16):1507-17). However, poor CAR T cell persistence and excessive T cell activation contribute to relapses and severe toxicities, respectively, and suggest a critical need to understand CAR T cell biology (Gangadhar, T. C. and R. H. Vonderheide, Nat Rev Clin Oncol, 2014. 11(2):91-9). Furthermore, relapses and toxicities have been seen with all second-generation CARs suggesting that the addition of co-stimulatory domains to CARs improved efficacy, but at the cost of biologic complications.

SUMMARY

As disclosed herein, CAR T cells with a CD28 co-stimulatory domain are prone to low-level tonic signaling and an exhaustion phenotype in CM cells, and mutating certain CD28 subdomains does not eliminate CAR signaling or cytokine production. Therefore, refinement of second-generation CAR T cell function can be achieved by modulating CD28 co-stimulation.

Disclosed herein are chimeric antigen receptor (CAR) polypeptides that can be used with adoptive cell transfer to target and kill cancers. The disclosed CARs comprise a costimulatory signaling region comprising a mutated form of the cytoplasmic domain of CD28 that enhances CAR-T cell function. In some embodiments, the mutated form reduces CAR-T cell exhaustion. The CD28 domain includes 3 intracellular subdomains (YMNM (SEQ ID NO:1), PRRP (SEQ ID NO:2), and PYAP (SEQ ID NO:3)) that regulate signaling pathways post TCR-stimulation. In some embodiments, the disclosed CAR comprises mutation or deletion of one or more of these subdomains that enhances CAR-T cell function, e.g. reducing CAR-T cell exhaustion. In some embodiments, the CAR polypeptides further comprise one or more deletions or mutations in CD3zeta and/or 41BB that enhance CAR T cell function.

As with other CARs, the disclosed CAR polypeptides contain in an ectodomain a ligand binding domain, such as an agent that can bind cancer cells expressing tumor associated antigen (TAA). The disclosed polypeptides can also contain a transmembrane domain and an endodomain capable of activating an immune effector cell. For example, the endodomain can contain an intracellular signaling domain and optionally one or more co-stimulatory signaling regions.

The ligand binding domain, e.g. anti-TAA binding agent, is in some embodiments an antibody fragment that specifically binds a TAA. For example, the antigen binding domain can be a Fab or a single-chain variable fragment (scFv) of an antibody that specifically binds a TAA. The anti-TAA binding agent is in some embodiments an aptamer that specifically binds the TAA. For example, the anti-TAA binding agent can be a peptide aptamer selected from a random sequence pool based on its ability to bind TAA. The anti-TAA binding agent can also be a natural ligand of TAA, or a variant and/or fragment thereof capable of binding the TAA.

In some embodiments, the intracellular signaling domain is a CD3 zeta (CD3ζ) signaling domain. In some cases, the costimulatory signaling region contains 1, 2, 3, or 4 cytoplasmic domains of one or more intracellular signaling molecules.

Also disclosed are isolated nucleic acid sequences encoding the disclosed CAR polypeptides, vectors comprising these isolated nucleic acids, and cells containing these vectors. For example, the cell can be an immune effector cell selected from the group consisting of an alpha-beta T cells, a gamma-delta T cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, and a regulatory T cell.

In some embodiments, the cell exhibits an anti-tumor immunity when the antigen binding domain of the CAR binds to the TAA on a tumor.

Also disclosed is a method of providing an anti-tumor immunity in a subject with a TAA-expressing cancer that involves administering to the subject an effective amount of an immune effector cell genetically modified with a disclosed TAA-specific CAR comprising a mutated CD28 co-stimulatory domain.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A is a schematic of CD28 subdomain mutations that support CAR signaling in Nur77$^{GFP}$ derived CAR T cells. Shown are YMNM (SEQ ID NO:1), PRRP (SEQ ID NO:2), and PYAP (SEQ ID NO:3) sequences replaced with AAAA (SEQ ID NO:4).

FIGS. 6A to 6D are bar graphs showing IFN-γ (FIG. 6A), IL-6 (FIG. 6B), IL-12 (FIG. 6C), and TNF-α (FIG. 6D) produced by mutated and non-mutated CAR T cells. CAR T cells were activated with 3T3-mCD19 cells at a ratio of 10:1. After 24 hrs supernatants were harvested and cytokines measured by Luminex kit.

FIGS. 9A to 9D are plots showing B cell killing (FIGS. 9A and 9C) and CAR T cell counts (FIGS. 9B, and 9D) in bone marrow (FIGS. 9A and 9B) and spleen (FIGS. 9C and 9D). 1×10$^6$ CAR T cells (CD3+ CAR+) were i.v. injected into cytoxan (300 mg/kg) pretreated wild type C57BL/6 mice. At week 8 bone marrow (BM) and spleens were collected and B cell and CAR T cell counts were analyzed by flow cytometry.

DETAILED DESCRIPTION

Figure 1:
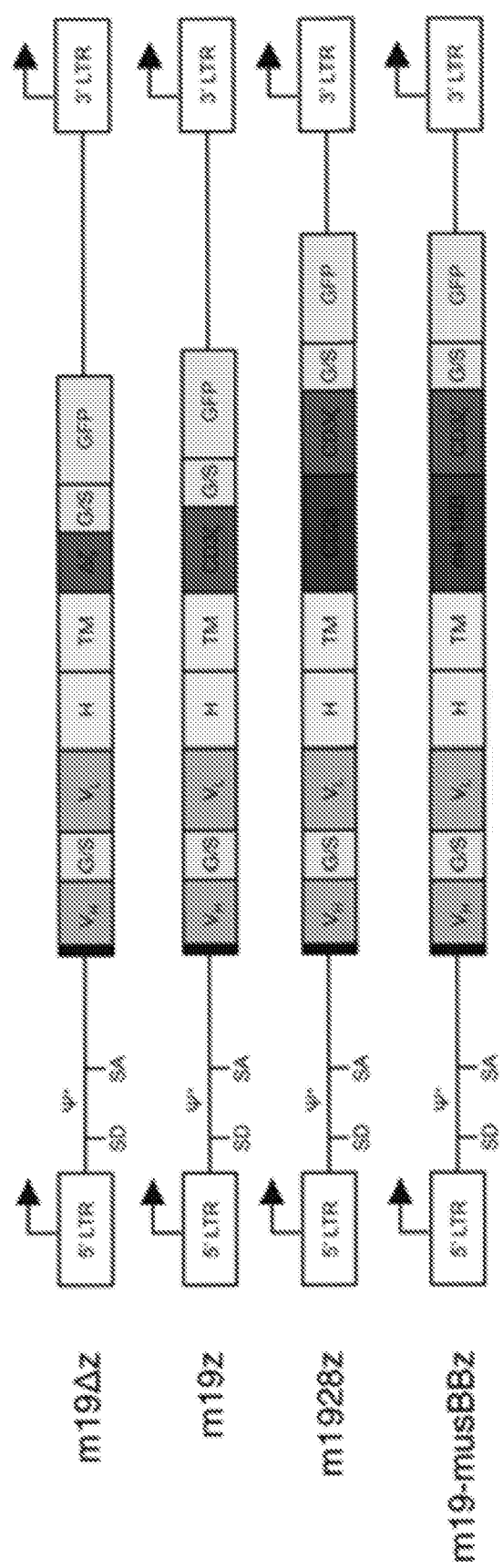
FIG. 1 is a schematic of anti-mouse CD19 CAR constructs. The retroviral constructs include an anti-mCD19 scFv (VH/VL) with a CD8 hinge (H) and transmembrane domain (TM) followed by CD28 (m1928z) or 41BB (m19-musBBz) and CD3ζ or CD3 ζ (alone (m19z). A negative control CAR includes no signaling domains (m19Δz). G/S is glycine-serine linker. The CAR is tagged to a fluorescent protein reporter (GFP or Cherry). LTR is long terminal repeat SD is splice-donor, SA is splice acceptor, and y is packaging signal.

Disclosed herein are chimeric antigen receptors (CARs) that can specifically recognize tumor-associated antigens (TAA) on cancers that comprise a mutated form of the cytoplasmic domain of CD28 that reduce CAR-T cell exhaustion. Also disclosed are immune effector cells, such as T cells or Natural Killer (NK) cells, that are engineered to express these CARs. Therefore, also disclosed are methods for providing an anti-tumor immunity in a subject with TAA-expressing cancers that involves adoptive transfer of the disclosed immune effector cells engineered to express the disclosed CARs.

Chimeric Antigen Receptors (CAR) with Mutated CD28 Domains

CARs generally incorporate an antigen recognition domain from the single-chain variable fragments (scFv) of a monoclonal antibody (mAb) with transmembrane signaling motifs involved in lymphocyte activation (Sadelain M, et al. Nat Rev Cancer 2003 3:35-45). Disclosed herein is a chimeric antigen receptor (CAR) that can be that can be expressed in immune effector cells to enhance antitumor activity against cancers.

The disclosed CAR is generally made up of three domains: an ectodomain, a transmembrane domain, and an endodomain. The ectodomain comprises the TAA-binding region and is responsible for antigen recognition. It also optionally contains a signal peptide (SP) so that the CAR can be glycosylated and anchored in the cell membrane of the immune effector cell. The transmembrane domain (TD), is as its name suggests, connects the ectodomain to the endodomain and resides within the cell membrane when expressed by a cell. The endodomain is the business end of the CAR that transmits an activation signal to the immune effector cell after antigen recognition. For example, the endodomain can contain an intracellular signaling domain (ISD) and a co-stimulatory signaling region (CSR).

The disclosed CARs have a CSR comprising a mutated form of CD28 that reduce CAR-T cell exhaustion. The CD28 domain includes 3 intracellular subdomains (YMNM (SEQ ID NO:1), PRRP (SEQ ID NO:2), and PYAP (SEQ ID NO:3)) that regulate signaling pathways post TCR-stimulation. In some embodiments, the disclosed CAR comprises mutation or deletion of one or more of these subdomains.

In some embodiments, the disclosed CAR is defined by the formula:

SP-TAA-HG-TM-CSR-ISD;

wherein "SP" represents an optional signal peptide,
wherein "TAA" represents a TAA-binding region,
wherein "HG" represents an optional hinge domain, wherein "TM" represents a transmembrane domain,
wherein "CSR" represents the co-stimulatory signaling region,
wherein "ISD" represents an intracellular signaling domain, and
wherein "-" represents a peptide bond or linker.

Additional CAR constructs are described, for example, in Fresnak A D, et al. Engineered T cells: the promise and challenges of cancer immunotherapy. Nat Rev Cancer. 2016 Aug. 23; 16(9):566-81, which is incorporated by reference in its entirety for the teaching of these CAR models.

For example, the CAR can be a TRUCK, Universal CAR, Self-driving CAR, Armored CAR, Self-destruct CAR, Conditional CAR, Marked CAR, TenCAR, Dual CAR, or sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (for example, cytotoxic T lymphocyte-associated antigen 4 (CTLA4) or programmed cell death protein 1 (PD1)), with an immune checkpoint switch receptor, or may be administered with a monoclonal antibody that blocks immune checkpoint signaling.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the circuit, enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets; one CAR includes only the CD3ζ domain and the other CAR includes only the co-stimulatory domain(s). Dual CAR T cell activation requires co-expression of both targets on the tumor.

A safety CAR (sCAR) consists of an extracellular scFv fused to an intracellular inhibitory domain, sCAR T cells co-expressing a standard CAR become activated only when encountering target cells that possess the standard CAR target but lack the sCAR target.

The antigen recognition domain of the disclosed CAR is usually an scFv. There are however many alternatives. An antigen recognition domain from native T-cell receptor (TCR) alpha and beta single chains have been described, as have simple ectodomains (e.g. CD4 ectodomain to recognize HIV infected cells) and more exotic recognition components such as a linked cytokine (which leads to recognition of cells bearing the cytokine receptor). In fact almost anything that binds a given target with high affinity can be used as an antigen recognition region.

The endodomain is the business end of the CAR that after antigen recognition transmits a signal to the immune effector cell, activating at least one of the normal effector functions of the immune effector cell. Effector function of a T cell, for example, may be cytolytic activity or helper activity including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM containing cytoplasmic signaling sequences include those derived from CD8, CD3ζ, CD3δ, CD3γ, CD3ε, CD32 (Fc gamma RIIa), DAP10, DAP12, CD79a, CD79b, FcγRIγ, FcγRIIIγ, FcεRIβ (FCERIB), and FcεRIγ (FCERIG).

In particular embodiments, the intracellular signaling domain is derived from CD3 zeta (CD3ζ) (TCR zeta, GenBank accno. BAG36664.1). T-cell surface glycoprotein CD3 zeta (CD3ζ) chain, also known as T-cell receptor T3 zeta chain or CD247 (Cluster of Differentiation 247), is a protein that in humans is encoded by the CD247 gene.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety and the transmembrane domain. The hinge sequence can be any suitable sequence derived or obtained from any suitable molecule. In some embodiments, for example, the hinge sequence is derived from a CD8a molecule or a CD28 molecule.

The transmembrane domain may be derived either from a natural or from a synthetic source. Where the source is natural, the domain may be derived from any membrane-bound or transmembrane protein. For example, the transmembrane region may be derived from (i.e. comprise at least the transmembrane region(s) of) the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp. Alternatively the transmembrane domain may be synthetic, in which case it will comprise predominantly hydrophobic residues such as leucine and valine. In some cases, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FCERI alpha chain and a part of an FCERI beta chain such that the FCERI chains spontaneously dimerize together to form a CAR.

Tables and 2 below provide some example combinations of TAA-binding region, co-stimulatory signaling regions, and intracellular signaling domain that can occur in the disclosed CARs.

TABLE 1

Second Generation CARs

| ScFv | Co-stimulatory Signal | Signal Domain |
|---|---|---|
| TAA | CD28* | CD8 |
| TAA | CD28* | CD3ζ |
| TAA | CD28* | CD3δ |
| TAA | CD28* | CD3γ |
| TAA | CD28* | CD3ε |
| TAA | CD28* | FcγRI-γ |
| TAA | CD28* | FcγRIII-γ |
| TAA | CD28* | FcεRIβ |
| TAA | CD28* | FcεRIγ |
| TAA | CD28* | DAP10 |
| TAA | CD28* | DAP12 |
| TAA | CD28* | CD32 |
| TAA | CD28* | CD79a |
| TAA | CD28* | CD79b |

CD28* = mutated CD28 co-stimulatory domain as described herein

TABLE 2

Third Generation CARs

| ScFv | Co-stimulatory Signal | Co-stimulatory Signal | Signal Domain |
|---|---|---|---|
| TAA | CD28* | CD28* | CD8 |
| TAA | CD28* | CD28* | CD3ζ |
| TAA | CD28* | CD28* | CD3δ |
| TAA | CD28* | CD28* | CD3γ |
| TAA | CD28* | CD28* | CD3ε |
| TAA | CD28* | CD28* | FcγRI-γ |
| TAA | CD28* | CD28* | FcγRIII-γ |
| TAA | CD28* | CD28* | FcεRIβ |
| TAA | CD28* | CD28* | FcεRIγ |
| TAA | CD28* | CD28* | DAP10 |
| TAA | CD28* | CD28* | DAP12 |
| TAA | CD28* | CD28* | CD32 |
| TAA | CD28* | CD28* | CD79a |
| TAA | CD28* | CD28* | CD79b |
| TAA | CD28* | CD8 | CD8 |
| TAA | CD28* | CD8 | CD3ζ |
| TAA | CD28* | CD8 | CD3δ |
| TAA | CD28* | CD8 | CD3γ |
| TAA | CD28* | CD8 | CD3ε |
| TAA | CD28* | CD8 | FcγRI-γ |
| TAA | CD28* | CD8 | FcγRIII-γ |
| TAA | CD28* | CD8 | FcεRIβ |
| TAA | CD28* | CD8 | FcεRIγ |
| TAA | CD28* | CD8 | DAP10 |
| TAA | CD28* | CD8 | DAP12 |
| TAA | CD28* | CD8 | CD32 |
| TAA | CD28* | CD8 | CD79a |
| TAA | CD28* | CD8 | CD79b |
| TAA | CD28* | CD4 | CD8 |
| TAA | CD28* | CD4 | CD3ζ |
| TAA | CD28* | CD4 | CD3δ |
| TAA | CD28* | CD4 | CD3γ |
| TAA | CD28* | CD4 | CD3ε |
| TAA | CD28* | CD4 | FcγRI-γ |
| TAA | CD28* | CD4 | FcγRIII-γ |
| TAA | CD28* | CD4 | FcεRIβ |
| TAA | CD28* | CD4 | FcεRIγ |
| TAA | CD28* | CD4 | DAP10 |
| TAA | CD28* | CD4 | DAP12 |
| TAA | CD28* | CD4 | CD32 |

TABLE 2-continued

Third Generation CARs

| ScFv | Co-stimulatory Signal | Co-stimulatory Signal | Signal Domain |
|---|---|---|---|
| TAA | CD28* | CD4 | CD79a |
| TAA | CD28* | CD4 | CD79b |
| TAA | CD28* | b2c | CD8 |
| TAA | CD28* | b2c | CD3ζ |
| TAA | CD28* | b2c | CD3δ |
| TAA | CD28* | b2c | CD3γ |
| TAA | CD28* | b2c | CD3ε |
| TAA | CD28* | b2c | FcγRI-γ |
| TAA | CD28* | b2c | FcγRIII-γ |
| TAA | CD28* | b2c | FcεRIβ |
| TAA | CD28* | b2c | FcεRIγ |
| TAA | CD28* | b2c | DAP10 |
| TAA | CD28* | b2c | DAP12 |
| TAA | CD28* | b2c | CD32 |
| TAA | CD28* | b2c | CD79a |
| TAA | CD28* | b2c | CD79b |
| TAA | CD28* | CD137/41BB | CD8 |
| TAA | CD28* | CD137/41BB | CD3ζ |
| TAA | CD28* | CD137/41BB | CD3δ |
| TAA | CD28* | CD137/41BB | CD3γ |
| TAA | CD28* | CD137/41BB | CD3ε |
| TAA | CD28* | CD137/41BB | FcγRI-γ |
| TAA | CD28* | CD137/41BB | FcγRIII-γ |
| TAA | CD28* | CD137/41BB | FcεRIβ |
| TAA | CD28* | CD137/41BB | FcεRIγ |
| TAA | CD28* | CD137/41BB | DAP10 |
| TAA | CD28* | CD137/41BB | DAP12 |
| TAA | CD28* | CD137/41BB | CD32 |
| TAA | CD28* | CD137/41BB | CD79a |
| TAA | CD28* | CD137/41BB | CD79b |
| TAA | CD28* | ICOS | CD8 |
| TAA | CD28* | ICOS | CD3ζ |
| TAA | CD28* | ICOS | CD3δ |
| TAA | CD28* | ICOS | CD3γ |
| TAA | CD28* | ICOS | CD3ε |
| TAA | CD28* | ICOS | FcγRI-γ |
| TAA | CD28* | ICOS | FcγRIII-γ |
| TAA | CD28* | ICOS | FcεRIβ |
| TAA | CD28* | ICOS | FcεRIγ |
| TAA | CD28* | ICOS | DAP10 |
| TAA | CD28* | ICOS | DAP12 |
| TAA | CD28* | ICOS | CD32 |
| TAA | CD28* | ICOS | CD79a |
| TAA | CD28* | ICOS | CD79b |
| TAA | CD28* | CD27 | CD8 |
| TAA | CD28* | CD27 | CD3ζ |
| TAA | CD28* | CD27 | CD3δ |
| TAA | CD28* | CD27 | CD3γ |
| TAA | CD28* | CD27 | CD3ε |
| TAA | CD28* | CD27 | FcγRI-γ |
| TAA | CD28* | CD27 | FcγRIII-γ |
| TAA | CD28* | CD27 | FcεRIβ |
| TAA | CD28* | CD27 | FcεRIγ |
| TAA | CD28* | CD27 | DAP10 |
| TAA | CD28* | CD27 | DAP12 |
| TAA | CD28* | CD27 | CD32 |
| TAA | CD28* | CD27 | CD79a |
| TAA | CD28* | CD27 | CD79b |
| TAA | CD28* | CD280 | CD8 |
| TAA | CD28* | CD280 | CD3ζ |
| TAA | CD28* | CD280 | CD3δ |
| TAA | CD28* | CD280 | CD3γ |
| TAA | CD28* | CD280 | CD3ε |
| TAA | CD28* | CD280 | FcγRI-γ |
| TAA | CD28* | CD280 | FcγRIII-γ |
| TAA | CD28* | CD280 | FcεRIβ |
| TAA | CD28* | CD286 | FcεRIγ |
| TAA | CD28* | CD286 | DAP10 |
| TAA | CD28* | CD286 | DAP12 |
| TAA | CD28* | CD286 | CD32 |
| TAA | CD28* | CD286 | CD79a |
| TAA | CD28* | CD286 | CD79b |
| TAA | CD28* | CD80 | CD8 |
| TAA | CD28* | CD80 | CD3ζ |
| TAA | CD28* | CD80 | CD3δ |
| TAA | CD28* | CD80 | CD3γ |
| TAA | CD28* | CD80 | CD3ε |
| TAA | CD28* | CD80 | FcγRI-γ |
| TAA | CD28* | CD80 | FcγRIII-γ |
| TAA | CD28* | CD80 | FcεRIβ |
| TAA | CD28* | CD80 | FcεRIγ |
| TAA | CD28* | CD80 | DAP10 |
| TAA | CD28* | CD80 | DAP12 |
| TAA | CD28* | CD80 | CD32 |
| TAA | CD28* | CD80 | CD79a |
| TAA | CD28* | CD80 | CD79b |
| TAA | CD28* | CD86 | CD8 |
| TAA | CD28* | CD86 | CD3ζ |
| TAA | CD28* | CD86 | CD3δ |
| TAA | CD28* | CD86 | CD3γ |
| TAA | CD28* | CD86 | CD3ε |
| TAA | CD28* | CD86 | FcγRI-γ |
| TAA | CD28* | CD86 | FcγRIII-γ |
| TAA | CD28* | CD86 | FcεRIβ |
| TAA | CD28* | CD86 | FcεRIγ |
| TAA | CD28* | CD86 | DAP10 |
| TAA | CD28* | CD86 | DAP12 |
| TAA | CD28* | CD86 | CD32 |
| TAA | CD28* | CD86 | CD79a |
| TAA | CD28* | CD86 | CD79b |
| TAA | CD28* | OX40 | CD8 |
| TAA | CD28* | OX40 | CD3ζ |
| TAA | CD28* | OX40 | CD3δ |
| TAA | CD28* | OX40 | CD3γ |
| TAA | CD28* | OX40 | CD3ε |
| TAA | CD28* | OX40 | FcγRI-γ |
| TAA | CD28* | OX40 | FcγRIII-γ |
| TAA | CD28* | OX40 | FcεRIβ |
| TAA | CD28* | OX40 | FcεRIγ |
| TAA | CD28* | OX40 | DAP10 |
| TAA | CD28* | OX40 | DAP12 |
| TAA | CD28* | OX40 | CD32 |
| TAA | CD28* | OX40 | CD79a |
| TAA | CD28* | OX40 | CD79b |
| TAA | CD28* | DAP10 | CD8 |
| TAA | CD28* | DAP10 | CD3ζ |
| TAA | CD28* | DAP10 | CD3δ |
| TAA | CD28* | DAP10 | CD3γ |
| TAA | CD28* | DAP10 | CD3ε |
| TAA | CD28* | DAP10 | FcγRI-γ |
| TAA | CD28* | DAP10 | FcγRIII-γ |
| TAA | CD28* | DAP10 | FcεRIβ |
| TAA | CD28* | DAP10 | FcεRIγ |
| TAA | CD28* | DAP10 | DAP10 |
| TAA | CD28* | DAP10 | DAP12 |
| TAA | CD28* | DAP10 | CD32 |
| TAA | CD28* | DAP10 | CD79a |
| TAA | CD28* | DAP10 | CD79b |
| TAA | CD28* | DAP12 | CD8 |
| TAA | CD28* | DAP12 | CD3ζ |
| TAA | CD28* | DAP12 | CD3δ |
| TAA | CD28* | DAP12 | CD3γ |
| TAA | CD28* | DAP12 | CD3ε |
| TAA | CD28* | DAP12 | FcγRI-γ |
| TAA | CD28* | DAP12 | FcγRIII-γ |
| TAA | CD28* | DAP12 | FcεRIβ |
| TAA | CD28* | DAP12 | FcεRIγ |
| TAA | CD28* | DAP12 | DAP10 |
| TAA | CD28* | DAP12 | DAP12 |
| TAA | CD28* | DAP12 | CD32 |
| TAA | CD28* | DAP12 | CD79a |
| TAA | CD28* | DAP12 | CD79b |
| TAA | CD28* | MyD88 | CD8 |
| TAA | CD28* | MyD88 | CD3ζ |
| TAA | CD28* | MyD88 | CD3δ |
| TAA | CD28* | MyD88 | CD3γ |
| TAA | CD28* | MyD88 | CD3ε |
| TAA | CD28* | MyD88 | FcγRI-γ |
| TAA | CD28* | MyD88 | FcγRIII-γ |
| TAA | CD28* | MyD88 | FcεRIβ |

TABLE 2-continued

Third Generation CARs

| ScFv | Co-stimulatory Signal | Co-stimulatory Signal | Signal Domain |
|---|---|---|---|
| TAA | CD28* | MyD88 | FcεRIγ |
| TAA | CD28* | MyD88 | DAP10 |
| TAA | CD28* | MyD88 | DAP12 |
| TAA | CD28* | MyD88 | CD32 |
| TAA | CD28* | MyD88 | CD79a |
| TAA | CD28* | MyD88 | CD79b |
| TAA | CD28* | CD7 | CD8 |
| TAA | CD28* | CD7 | CD3ζ |
| TAA | CD28* | CD7 | CD3δ |
| TAA | CD28* | CD7 | CD3γ |
| TAA | CD28* | CD7 | CD3ε |
| TAA | CD28* | CD7 | FcγRI-γ |
| TAA | CD28* | CD7 | FcγRIII-γ |
| TAA | CD28* | CD7 | FcεRIβ |
| TAA | CD28* | CD7 | FcεRIγ |
| TAA | CD28* | CD7 | DAP10 |
| TAA | CD28* | CD7 | DAP12 |
| TAA | CD28* | CD7 | CD32 |
| TAA | CD28* | CD7 | CD79a |
| TAA | CD28* | CD7 | CD79b |
| TAA | CD28* | BTNL3 | CD8 |
| TAA | CD28* | BTNL3 | CD3ζ |
| TAA | CD28* | BTNL3 | CD3δ |
| TAA | CD28* | BTNL3 | CD3γ |
| TAA | CD28* | BTNL3 | CD3ε |
| TAA | CD28* | BTNL3 | FcγRI-γ |
| TAA | CD28* | BTNL3 | FcγRIII-γ |
| TAA | CD28* | BTNL3 | FcεRIβ |
| TAA | CD28* | BTNL3 | FcεRIγ |
| TAA | CD28* | BTNL3 | DAP10 |
| TAA | CD28* | BTNL3 | DAP12 |
| TAA | CD28* | BTNL3 | CD32 |
| TAA | CD28* | BTNL3 | CD79a |
| TAA | CD28* | BTNL3 | CD79b |
| TAA | CD28* | NKG2D | CD8 |
| TAA | CD28* | NKG2D | CD3ζ |
| TAA | CD28* | NKG2D | CD3δ |
| TAA | CD28* | NKG2D | CD3γ |
| TAA | CD28* | NKG2D | CD3ε |
| TAA | CD28* | NKG2D | FcγRI-γ |
| TAA | CD28* | NKG2D | FcγRIII-γ |
| TAA | CD28* | NKG2D | FcεRIβ |
| TAA | CD28* | NKG2D | FcεRIγ |
| TAA | CD28* | NKG2D | DAP10 |
| TAA | CD28* | NKG2D | DAP12 |
| TAA | CD28* | NKG2D | CD32 |
| TAA | CD28* | NKG2D | CD79a |
| TAA | CD28* | NKG2D | CD79b |
| TAA | CD8 | CD28* | CD8 |
| TAA | CD8 | CD28* | CD3ζ |
| TAA | CD8 | CD28* | CD3δ |
| TAA | CD8 | CD28* | CD3γ |
| TAA | CD8 | CD28* | CD3ε |
| TAA | CD8 | CD28* | FcγRI-γ |
| TAA | CD8 | CD28* | FcγRIII-γ |
| TAA | CD8 | CD28* | FcεRIβ |
| TAA | CD8 | CD28* | FcεRIγ |
| TAA | CD8 | CD28* | DAP10 |
| TAA | CD8 | CD28* | DAP12 |
| TAA | CD8 | CD28* | CD32 |
| TAA | CD8 | CD28* | CD79a |
| TAA | CD8 | CD28* | CD79b |
| TAA | CD4 | CD28* | CD8 |
| TAA | CD4 | CD28* | CD3ζ |
| TAA | CD4 | CD28* | CD3δ |
| TAA | CD4 | CD28* | CD3γ |
| TAA | CD4 | CD28* | CD3ε |
| TAA | CD4 | CD28* | FcγRI-γ |
| TAA | CD4 | CD28* | FcγRIII-γ |
| TAA | CD4 | CD28* | FcεRIβ |
| TAA | CD4 | CD28* | FcεRIγ |
| TAA | CD4 | CD28* | DAP10 |
| TAA | CD4 | CD28* | DAP12 |
| TAA | CD4 | CD28* | CD32 |
| TAA | CD4 | CD28* | CD79a |
| TAA | CD4 | CD28* | CD79b |
| TAA | b2c | CD28* | CD8 |
| TAA | b2c | CD28* | CD3ζ |
| TAA | b2c | CD28* | CD3δ |
| TAA | b2c | CD28* | CD3γ |
| TAA | b2c | CD28* | CD3ε |
| TAA | b2c | CD28* | FcγRI-γ |
| TAA | b2c | CD28* | FcγRIII-γ |
| TAA | b2c | CD28* | FcεRIβ |
| TAA | b2c | CD28* | FcεRIγ |
| TAA | b2c | CD28* | DAP10 |
| TAA | b2c | CD28* | DAP12 |
| TAA | b2c | CD28* | CD32 |
| TAA | b2c | CD28* | CD79a |
| TAA | b2c | CD28* | CD79b |
| TAA | CD137/41BB | CD28* | CD8 |
| TAA | CD137/41BB | CD28* | CD3ζ |
| TAA | CD137/41BB | CD28* | CD3δ |
| TAA | CD137/41BB | CD28* | CD3γ |
| TAA | CD137/41BB | CD28* | CD3ε |
| TAA | CD137/41BB | CD28* | FcγRI-γ |
| TAA | CD137/41BB | CD28* | FcγRIII-γ |
| TAA | CD137/41BB | CD28* | FcεRIβ |
| TAA | CD137/41BB | CD28* | FcεRIγ |
| TAA | CD137/41BB | CD28* | DAP10 |
| TAA | CD137/41BB | CD28* | DAP12 |
| TAA | CD137/41BB | CD28* | CD32 |
| TAA | CD137/41BB | CD28* | CD79a |
| TAA | CD137/41BB | CD28* | CD79b |
| TAA | ICOS | CD28* | CD8 |
| TAA | ICOS | CD28* | CD3ζ |
| TAA | ICOS | CD28* | CD3δ |
| TAA | ICOS | CD28* | CD3γ |
| TAA | ICOS | CD28* | CD3ε |
| TAA | ICOS | CD28* | FcγRI-γ |
| TAA | ICOS | CD28* | FcγRIII-γ |
| TAA | ICOS | CD28* | FcεRIβ |
| TAA | ICOS | CD28* | FcεRIγ |
| TAA | ICOS | CD28* | DAP10 |
| TAA | ICOS | CD28* | DAP12 |
| TAA | ICOS | CD28* | CD32 |
| TAA | ICOS | CD28* | CD79a |
| TAA | ICOS | CD28* | CD79b |
| TAA | CD27 | CD28* | CD8 |
| TAA | CD27 | CD28* | CD3ζ |
| TAA | CD27 | CD28* | CD3δ |
| TAA | CD27 | CD28* | CD3γ |
| TAA | CD27 | CD28* | CD3ε |
| TAA | CD27 | CD28* | FcγRI-γ |
| TAA | CD27 | CD28* | FcγRIII-γ |
| TAA | CD27 | CD28* | FcεRIβ |
| TAA | CD27 | CD28* | FcεRIγ |
| TAA | CD27 | CD28* | DAP10 |
| TAA | CD27 | CD28* | DAP12 |
| TAA | CD27 | CD28* | CD32 |
| TAA | CD27 | CD28* | CD79a |
| TAA | CD27 | CD28* | CD79b |
| TAA | CD28δ | CD28* | CD8 |
| TAA | CD28δ | CD28* | CD3ζ |
| TAA | CD28δ | CD28* | CD3δ |
| TAA | CD28δ | CD28* | CD3γ |
| TAA | CD28δ | CD28* | CD3ε |
| TAA | CD28δ | CD28* | FcγRI-γ |
| TAA | CD28δ | CD28* | FcγRIII-γ |
| TAA | CD28δ | CD28* | FcεRIβ |
| TAA | CD28δ | CD28* | FcεRIγ |
| TAA | CD28δ | CD28* | DAP10 |
| TAA | CD28δ | CD28* | DAP12 |
| TAA | CD28δ | CD28* | CD32 |
| TAA | CD28δ | CD28* | CD79a |
| TAA | CD28δ | CD28* | CD79b |
| TAA | CD80 | CD28* | CD8 |
| TAA | CD80 | CD28* | CD3ζ |
| TAA | CD80 | CD28* | CD3δ |
| TAA | CD80 | CD28* | CD3γ |

TABLE 2-continued

Third Generation CARs

| ScFv | Co-stimulatory Signal | Co-stimulatory Signal | Signal Domain |
|---|---|---|---|
| TAA | CD80 | CD28* | CD3ε |
| TAA | CD80 | CD28* | FcγRI-γ |
| TAA | CD80 | CD28* | FcγRIII-γ |
| TAA | CD80 | CD28* | FcεRIβ |
| TAA | CD80 | CD28* | FcεRIγ |
| TAA | CD80 | CD28* | DAP10 |
| TAA | CD80 | CD28* | DAP12 |
| TAA | CD80 | CD28* | CD32 |
| TAA | CD80 | CD28* | CD79a |
| TAA | CD80 | CD28* | CD79b |
| TAA | CD86 | CD28* | CD8 |
| TAA | CD86 | CD28* | CD3ζ |
| TAA | CD86 | CD28* | CD3δ |
| TAA | CD86 | CD28* | CD3γ |
| TAA | CD86 | CD28* | CD3ε |
| TAA | CD86 | CD28* | FcγRI-γ |
| TAA | CD86 | CD28* | FcγRIII-γ |
| TAA | CD86 | CD28* | FcεRIβ |
| TAA | CD86 | CD28* | FcεRIγ |
| TAA | CD86 | CD28* | DAP10 |
| TAA | CD86 | CD28* | DAP12 |
| TAA | CD86 | CD28* | CD32 |
| TAA | CD86 | CD28* | CD79a |
| TAA | CD86 | CD28* | CD79b |
| TAA | OX40 | CD28* | CD8 |
| TAA | OX40 | CD28* | CD3ζ |
| TAA | OX40 | CD28* | CD3δ |
| TAA | OX40 | CD28* | CD3γ |
| TAA | OX40 | CD28* | CD3ε |
| TAA | OX40 | CD28* | FcγRI-γ |
| TAA | OX40 | CD28* | FcγRIII-γ |
| TAA | OX40 | CD28* | FcεRIβ |
| TAA | OX40 | CD28* | FcεRIγ |
| TAA | OX40 | CD28* | DAP10 |
| TAA | OX40 | CD28* | DAP12 |
| TAA | OX40 | CD28* | CD32 |
| TAA | OX40 | CD28* | CD79a |
| TAA | OX40 | CD28* | CD79b |
| TAA | DAP10 | CD28* | CD8 |
| TAA | DAP10 | CD28* | CD3ζ |
| TAA | DAP10 | CD28* | CD3δ |
| TAA | DAP10 | CD28* | CD3γ |
| TAA | DAP10 | CD28* | CD3ε |
| TAA | DAP10 | CD28* | FcγRI-γ |
| TAA | DAP10 | CD28* | FcγRIII-γ |
| TAA | DAP10 | CD28* | FcεRIβ |
| TAA | DAP10 | CD28* | FcεRIγ |
| TAA | DAP10 | CD28* | DAP10 |
| TAA | DAP10 | CD28* | DAP12 |
| TAA | DAP10 | CD28* | CD32 |
| TAA | DAP10 | CD28* | CD79a |
| TAA | DAP10 | CD28* | CD79b |
| TAA | DAP12 | CD28* | CD8 |
| TAA | DAP12 | CD28* | CD3ζ |
| TAA | DAP12 | CD28* | CD3δ |
| TAA | DAP12 | CD28* | CD3γ |
| TAA | DAP12 | CD28* | CD3ε |
| TAA | DAP12 | CD28* | FcγRI-γ |
| TAA | DAP12 | CD28* | FcγRIII-γ |
| TAA | DAP12 | CD28* | FcεRIβ |
| TAA | DAP12 | CD28* | FcεRIγ |
| TAA | DAP12 | CD28* | DAP10 |
| TAA | DAP12 | CD28* | DAP12 |
| TAA | DAP12 | CD28* | CD32 |
| TAA | DAP12 | CD28* | CD79a |
| TAA | DAP12 | CD28* | CD79b |
| TAA | MyD88 | CD28* | CD8 |
| TAA | MyD88 | CD28* | CD3ζ |
| TAA | MyD88 | CD28* | CD3δ |
| TAA | MyD88 | CD28* | CD3γ |
| TAA | MyD88 | CD28* | CD3ε |
| TAA | MyD88 | CD28* | FcγRI-γ |
| TAA | MyD88 | CD28* | FcγRIII-γ |
| TAA | MyD88 | CD28* | FcεRIβ |
| TAA | MyD88 | CD28* | FcεRIγ |
| TAA | MyD88 | CD28* | DAP10 |
| TAA | MyD88 | CD28* | DAP12 |
| TAA | MyD88 | CD28* | CD32 |
| TAA | MyD88 | CD28* | CD79a |
| TAA | MyD88 | CD28* | CD79b |
| TAA | CD7 | CD28* | CD8 |
| TAA | CD7 | CD28* | CD3ζ |
| TAA | CD7 | CD28* | CD3δ |
| TAA | CD7 | CD28* | CD3γ |
| TAA | CD7 | CD28* | CD3ε |
| TAA | CD7 | CD28* | FcγRI-γ |
| TAA | CD7 | CD28* | FcγRIII-γ |
| TAA | CD7 | CD28* | FcεRIβ |
| TAA | CD7 | CD28* | FcεRIγ |
| TAA | CD7 | CD28* | DAP10 |
| TAA | CD7 | CD28* | DAP12 |
| TAA | CD7 | CD28* | CD32 |
| TAA | CD7 | CD28* | CD79a |
| TAA | CD7 | CD28* | CD79b |
| TAA | BTNL3 | CD28* | CD8 |
| TAA | BTNL3 | CD28* | CD3ζ |
| TAA | BTNL3 | CD28* | CD3δ |
| TAA | BTNL3 | CD28* | CD3γ |
| TAA | BTNL3 | CD28* | CD3ε |
| TAA | BTNL3 | CD28* | FcγRI-γ |
| TAA | BTNL3 | CD28* | FcγRIII-γ |
| TAA | BTNL3 | CD28* | FcεRIβ |
| TAA | BTNL3 | CD28* | FcεRIγ |
| TAA | BTNL3 | CD28* | DAP10 |
| TAA | BTNL3 | CD28* | DAP12 |
| TAA | BTNL3 | CD28* | CD32 |
| TAA | BTNL3 | CD28* | CD79a |
| TAA | BTNL3 | CD28* | CD79b |
| TAA | NKG2D | CD28* | CD8 |
| TAA | NKG2D | CD28* | CD3ζ |
| TAA | NKG2D | CD28* | CD3δ |
| TAA | NKG2D | CD28* | CD3γ |
| TAA | NKG2D | CD28* | CD3ε |
| TAA | NKG2D | CD28* | FcγRI-γ |
| TAA | NKG2D | CD28* | FcγRIII-γ |
| TAA | NKG2D | CD28* | FcεRIβ |
| TAA | NKG2D | CD28* | FcεRIγ |
| TAA | NKG2D | CD28* | DAP10 |
| TAA | NKG2D | CD28* | DAP12 |
| TAA | NKG2D | CD28* | CD32 |
| TAA | NKG2D | CD28* | CD79a |
| TAA | NKG2D | CD28* | CD79b |

CD28* = mutated CD28 co-stimulatory domain as described herein

In some embodiments, the anti-TAA binding agent is single chain variable fragment (scFv) antibody. The affinity/specificity of an anti-TAA scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some cases, the anti-TAA binding agent is an affinity maturated scFv. In some cases, the anti-TAA has a dissociation constant ($K_D$) for the TAA that is less than 50 nM, 40 nM, 30 nM, 25 nM, 20 nM, 15 nM, or 10 nM.

In some embodiments, the anti-TAA binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, CD123, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-Ia, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, CD33, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, CD33, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Nucleic Acids and Vectors

Also disclosed are polynucleotides and polynucleotide vectors encoding the disclosed CARs that allow expression of the CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Expression of nucleic acids encoding CARs is typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells." These cells are preferably obtained from the subject to be treated (i.e. are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dentritic cells, mast cells, neutrophils, basophils, eosinophils, or any combinations thereof. For example, the immune effector cells can comprise T lymphocytes.

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, $T_H9$, or $T_{FH}$, which secrete different cytokines to facilitate a different type of immune response.

Cytotoxic T cells ($T_C$ cells, or CTLs) destroy virally infected cells and tumor cells, and are also implicated in transplant rejection. These cells are also known as CD8+ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8+ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either CD4+ or CD8+. Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4+ $T_{reg}$ cells have been described—naturally occurring $T_{reg}$ cells and adaptive $T_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4+ cells. In other embodiments, the T cells are enriched for one or more subsets based on cell surface expression. For example, in some cases, the T comprise are cytotoxic CD8+ T lymphocytes. In some embodiments, the T cells comprise γδ T cells, which possess a distinct T-cell receptor (TCR) having one γ chain and one δ chain instead of α and β chains.

Natural-killer (NK) cells are CD56+CD3− large granular lymphocytes that can kill virally infected and transformed cells, and constitute a critical cellular subset of the innate immune system (Godfrey J, et al. Leuk Lymphoma 2012 53:1666-1676). Unlike cytotoxic CD8+ T lymphocytes, NK cells launch cytotoxicity against tumor cells without the requirement for prior sensitization, and can also eradicate MHC-I-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects. Although NK cells have a well-known role as killers of cancer cells, and NK cell impairment has been extensively documented as crucial for progression of MM (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Therapeutic Methods

Immune effector cells expressing the disclosed CARs can elicit an anti-tumor immune response against TAA-expressing cancer cells. The anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to TAA.

Adoptive transfer of immune effector cells expressing chimeric antigen receptors is a promising anti-cancer therapeutic. Following the collection of a patient's immune effector cells, the cells may be genetically engineered to express the disclosed CARs, then infused back into the patient.

The disclosed CAR-modified immune effector cells may be administered either alone, or as a pharmaceutical composition in combination with diluents and/or with other components such as IL-2, IL-15, or other cytokines or cell populations. Briefly, pharmaceutical compositions may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The cancer of the disclosed methods can be any TAA-expressing cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The disclosed CARs can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed CARs can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MED14736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed CARs can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec ST1571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a CARs for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-Ia from the human CXC and C-C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with an CARs for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed CARs is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed CARs is administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines as cancer therapies are being investigated both pre-clinically and clinically, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-β (Dranoff 2004). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon 2011). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TILs (tumor infiltrating lymphocytes). While PD1-PDL1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-β receptor are resistant to the immunosuppression by lymphoma secreted TGF-β. These transduced cells showed notably increased antitumor activity in vivo when compared to their control counterparts.

Tandem and dual CAR-T cells are unique in that they possess two distinct antigen binding domains. A tandem CAR contains two sequential antigen binding domains facing the extracellular environment connected to the intracellular costimulatory and stimulatory domains. A dual CAR is engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC tag, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these extracellular domains is directed against a tumor related antigen and bound to an intracellular costimulatory and stimulatory domain. The second extracellular antigen binding domain however is specific for normal tissue and bound to an intracellular checkpoint domain such as CTLA4, PD1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tumor tissue, and is advantageous in situations where certain normal tissues may express very low levels of a tumor associated antigen that would lead to off target effects with a standard CAR (Morgan 2010). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason these too are also referred to as a "split CAR".

In some embodiments, two or more of these engineered features may be combined to create an enhanced, multifunctional CAR-T. For example, it is possible to create a CAR-T cell with either dual- or conditional-CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Typically, CAR-T cells are created using $\alpha$-$\beta$ T cells, however $\gamma$-$\delta$ T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In an additional embodiment, the transduced with CARs may be autologous or allogeneic.

Several different methods for CAR expression may be used including retroviral transduction (including $\gamma$-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

Definitions

The term "amino acid sequence" refers to a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "protein domain" refers to a portion of a protein, portions of a protein, or an entire protein showing structural integrity; this determination may be based on amino acid composition of a portion of a protein, portions of a protein, or the entire protein.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The terms "transformation" and "transfection" mean the introduction of a nucleic acid, e.g., an expression vector, into a recipient cell including introduction of a nucleic acid to the chromosomal DNA of said cell.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, nonconservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

A number of embodiments of the invention have been described. Nevertheless, it will be understood that various modifications may be made without departing from the spirit and scope of the invention. Accordingly, other embodiments are within the scope of the following claims.

EXAMPLES

Example 1

Figure 2B:
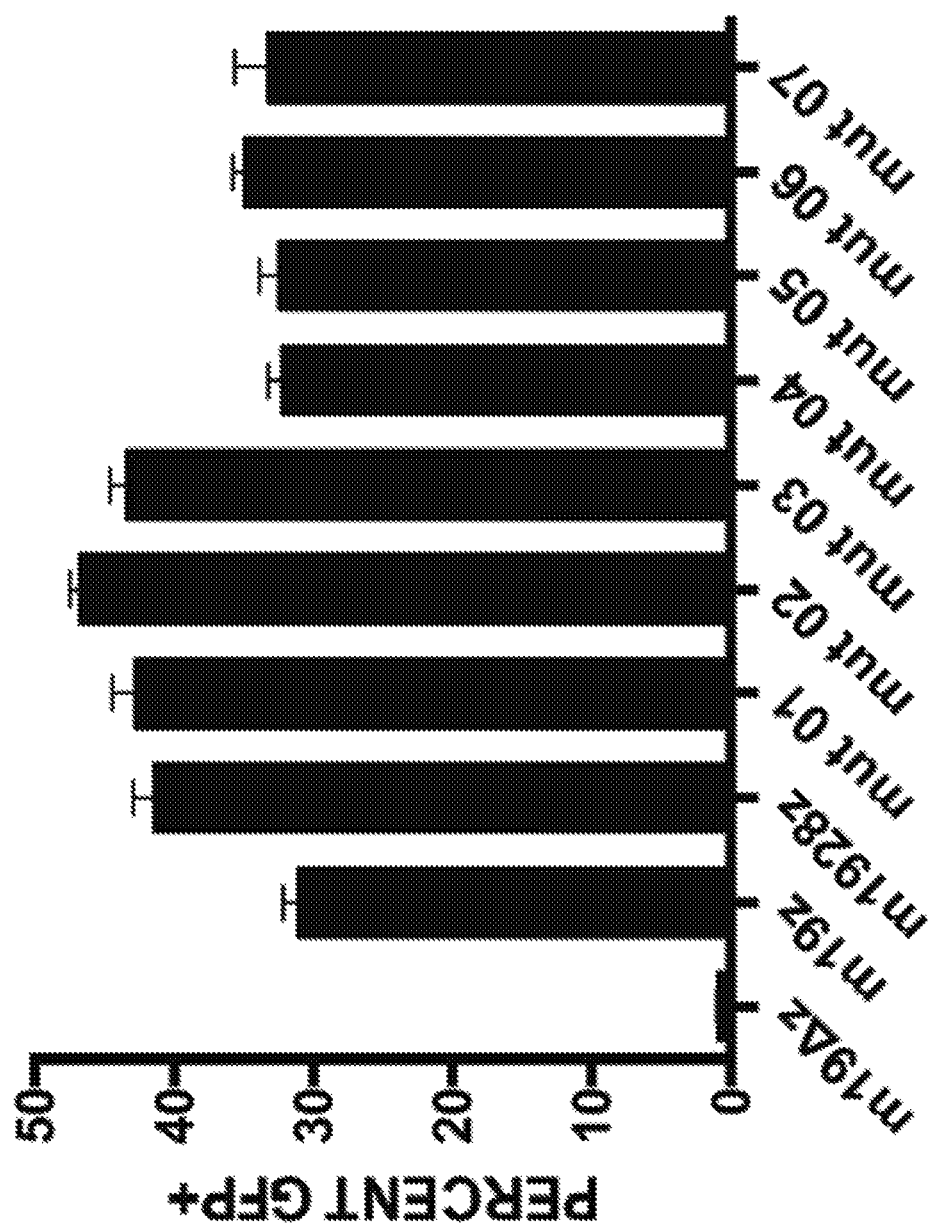
FIG. 2B is a bar graph showing Nur77$^{GFP}$ (percent GFP+) CD19-targeted CAR T cells stimulated with 3T3-mCD19. 24 hours after stimulation Nur77$^{GFP}$ was evaluated by flow cytometry.

Fully murine anti-mouse CD19 constructs were developed to validate B-ALL as a targeted for CD19-targeted CAR T cells (Davila et al., 2013 PLoS One 8:e61338). This included the 2nd generation m1928z CAR, which contains the CD28 costimulatory domain (FIG. 1). The CD28 costimulatory domain used in CAR T cells is from the cytoplasmic tail of CD28, which has no intrinsic enzymatic activity but contains subdomains or motifs that regulate T cell signaling. The YMNM (SEQ ID NO:1) motif is a binding site for the p85 subunit of PI3k and CD28 co-stimulation supports PI3k activation leading to cell cycle progression, anti-apoptosis, and cellular metabolism (Rudd and Schneider, 2003 Nat Rev Immunol 3:544-556; Sasaki et al., 2000 Science 287:1040-1046; Wang and Rudd, 2008 Trends Cell Biol 18:486-493). Studies of mice with a mutated YMNM (SEQ ID NO:1) domain abrogate PI3k signaling without other associated in vivo defects (Dodson et al., 2009). The PYAP (SEQ ID NO:3) motif of CD28 binds LCK resulting in T cell activation and IL2 production (Holdorf et al., 1999 J Exp Med 190:375-384; Kim et al., 1998 J Biol Chem 273:296-301). Other molecules with SH3 domains, including Fyn, Grb2, and GADS, also bind to the PYAP (SEQ ID NO:3) and PRRP (SEQ ID NO:2) motifs (Ellis et al., 2000 J Immunol 164:5805-5814; Okkenhaug and Rottapel, 1998 J Biol Chem 273:21194-21202). Mice with mutations in the PYAP (SEQ ID NO:3) domain have markedly impaired CD28-dependent proliferation, cytokine secretion, and adaptive immunity (Burr et al., 2001 J Immunol 166:5331-5335; Dodson et al., 2009 Mol Cell Biol 29:3710-3721; Friend et al., 2006 J Exp Med 203:2121-2133). Collectively, these results demonstrate that CD28 subdomains mediate distinct signaling and functional pathways and are differentially required for T cell function. In addition, CD28 is known to amplify low-level TCR signals (Acuto and Michel, 2003 Nat Rev Immunol 3:939-951) and data supports a model whereby low-level tonic CAR signaling is amplified by CD28 leading to CAR T cell exhaustion in vivo. It was unknown how these subdomains and their signaling pathways regulate CAR-T cell function so experiments were conducted to define their role and to design the optimal signaling construct for human translation. Therefore, a series of 7 mutants in the YMNM (SEQ ID NO:1), PRRP (SEQ ID NO:2), or PYAP (SEQ ID NO:3) subdomains were designed (FIG. 2A). These CAR constructs include either null mutations of a single subdomain (Mut01-Mut03) or 2 mutated subdomains leaving only a single functional subdomain (Mut04-Mu06). A triple mutant (Mut07) was also created with all 3 subdomains mutated. The CD28Mut CARs were evaluated in T cells from Nur77$^{GFP}$ mice and all supported CAR signaling was determined, although double mutants (Mut04-Mut06) had lower Nur77$^{GFP}$ at levels similar to the 1st generation m19z CAR (FIG. 14B). Using these CD28 mutants and other novel CAR designs the mechanism of CAR T cell exhaustion was evaluate by CD28 co-stimulation and methods to reduce exhaustion to enhance persistence were identified.

Figure 3A:
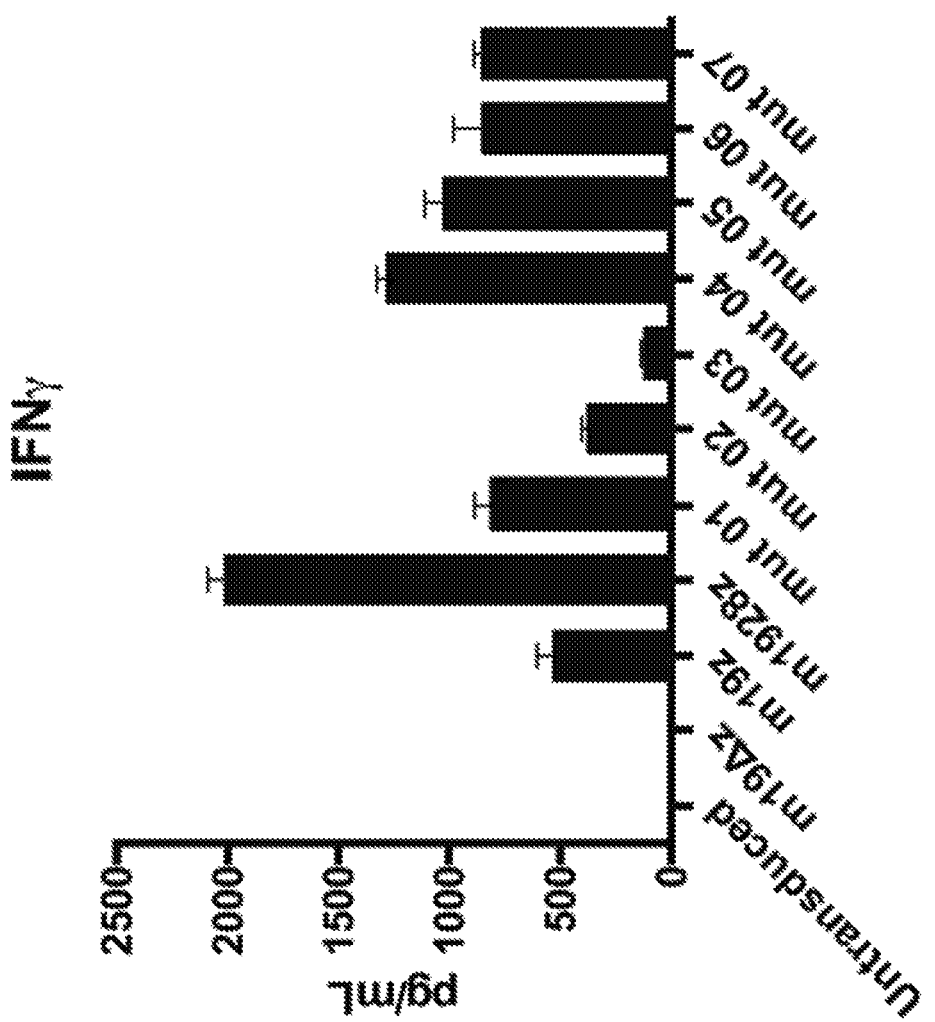
FIGS. 3A and 3B are bar graphs showing IFN-γ (FIG. 3A) and IL-2 (FIG. 3B) secretion after CD28 subdomain mutant CD19-targeted CAR T cells were stimulated with 3T3 cells that express mouse CD19 (3T3-mCD19).
Figure 3B:
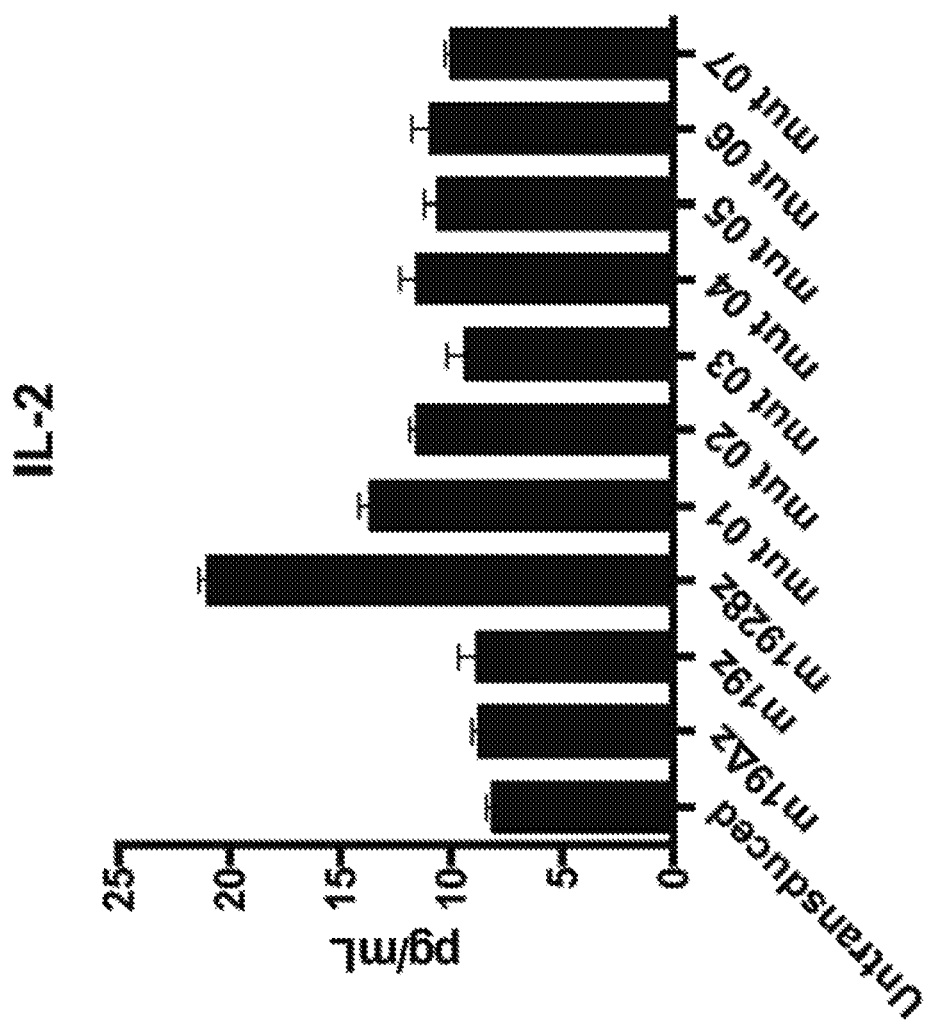
Figure 3C:
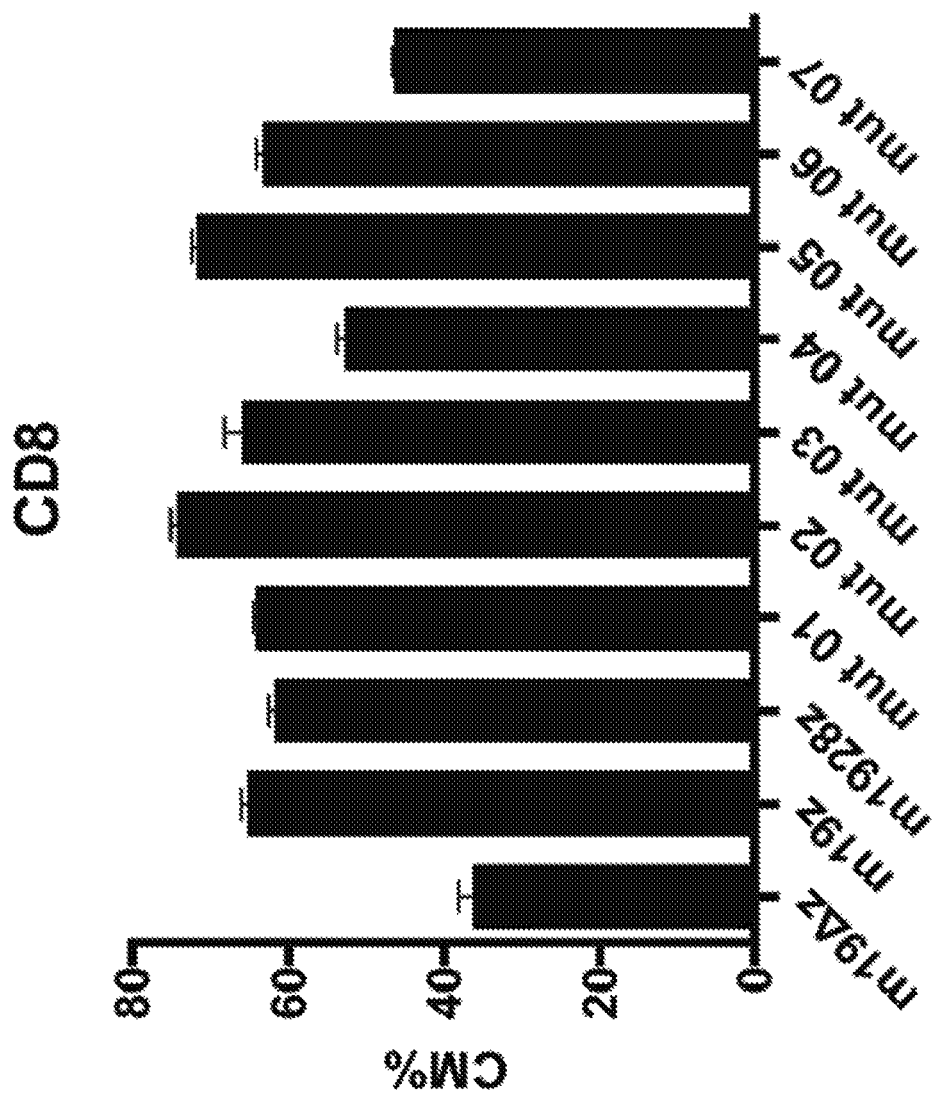
FIGS. 3C and 3D are bar graphs showing CM and EM subsets evaluated by flow cytometry.
Figure 3D:
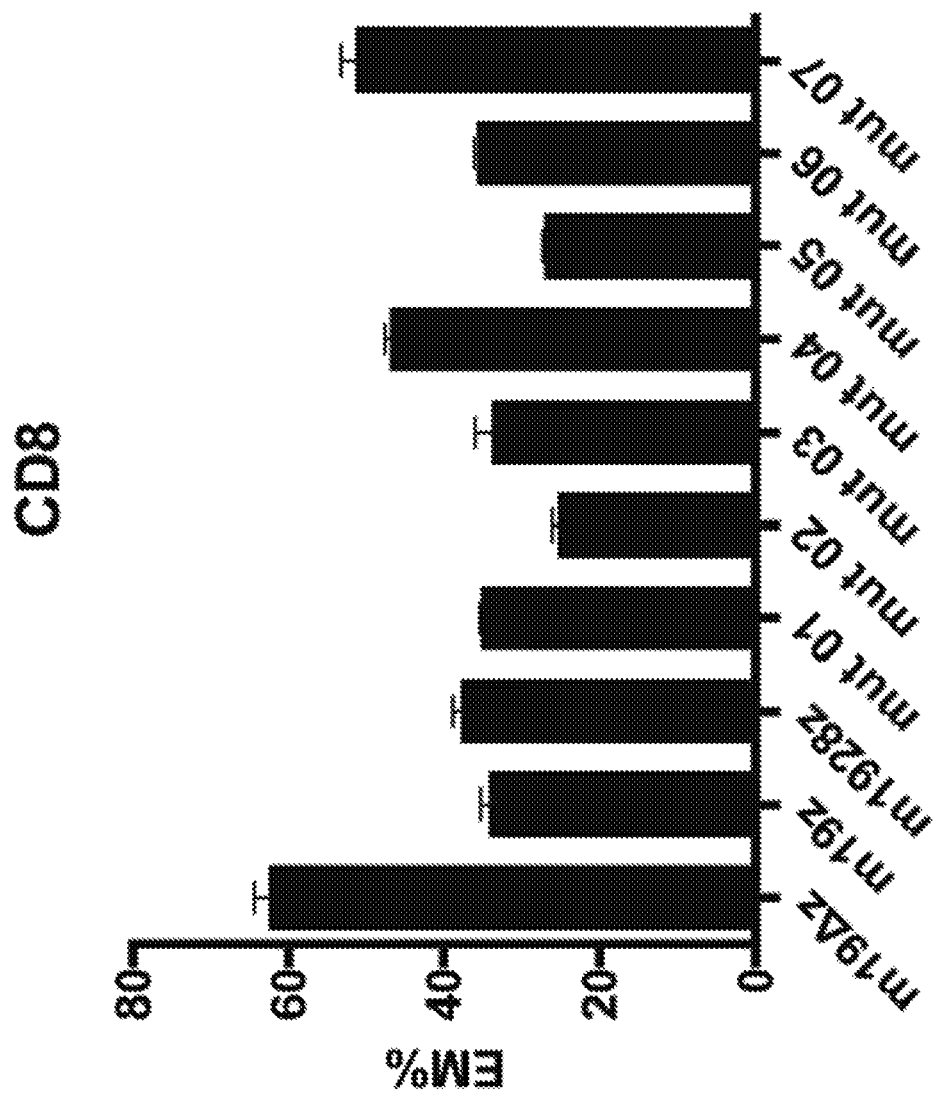

To determine the regulatory role of the CD28 co-stimulatory subdomains for in vitro and in vivo function of CD19-targeted CAR T cells, how each subdomain contributes to CAR T cell function was defined using CD28 mutants (FIG. 2A). The cytokine production and memory subsets of the CD28 mutant CAR T cells was evaluated, demonstrating that double mutants (Mut04-06) have enhanced IFNγ secretion compared to single mutants (Mut01-03), while all CD28 mutants produce similarly reduced levels of IL2 (FIG. 3A-B). CM and EM CAR T cell subsets were largely preserved, but with variable effects such as Mut04 having decreased CM and increased EM subsets (FIG. 3C-D). These results demonstrate differential outcomes in CD28 mutants, which may be related to the differential induction of transcriptional pathways such as AP1, NFAT, or NFKB. These modifications can serve as refinements in CAR design to improve response rates, reduce relapse relates, and most importantly, improve survival for patients with treatment-refractory cancer.

Example 2

Figure 4:
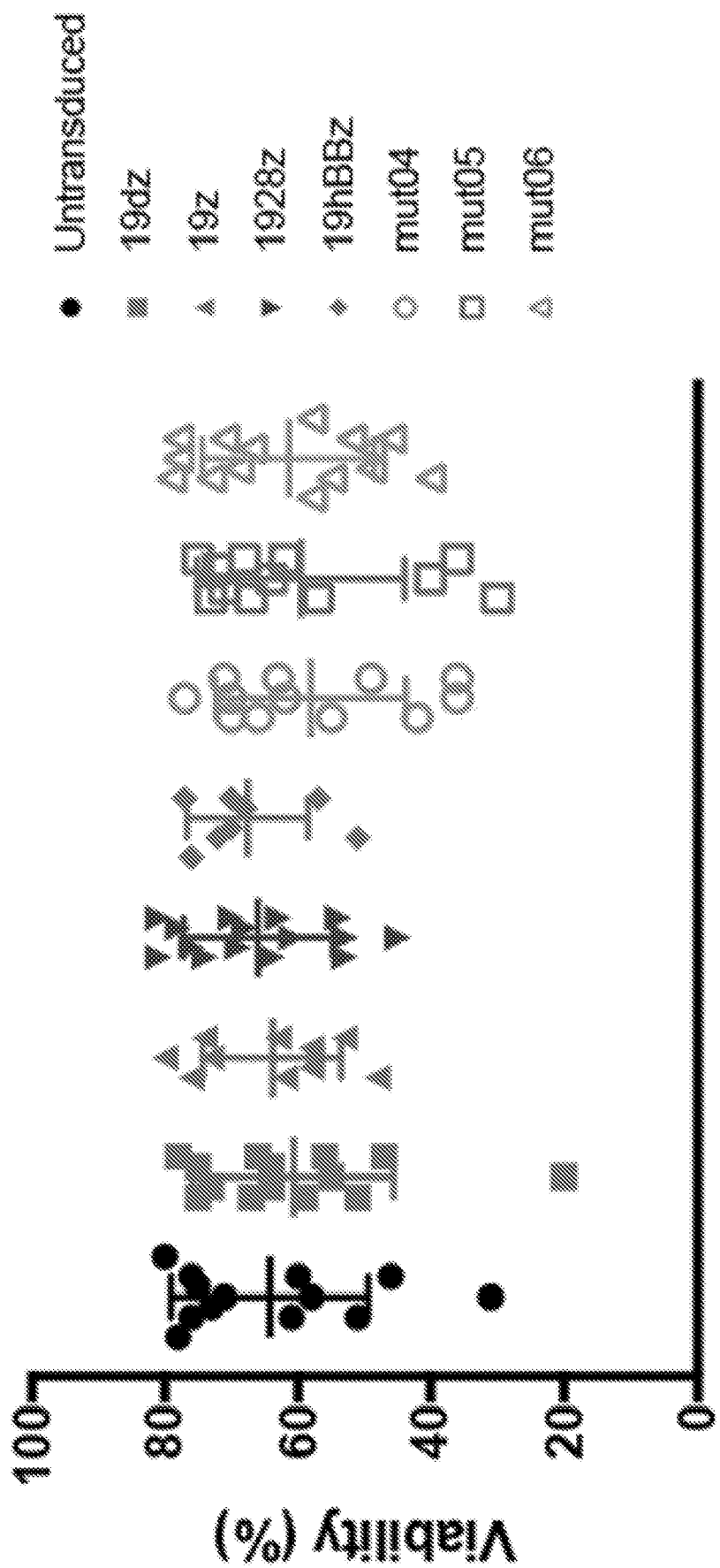
FIG. 4 is a plot showing viability of CD28 mutated CAR T cells and non-mutated CAR T cells. CAR T cells were produced from wild type C57BL/6 mice and cell viability was measured by trypan blue staining on an automated cell counter (BIO-RAD).
Figure 5:
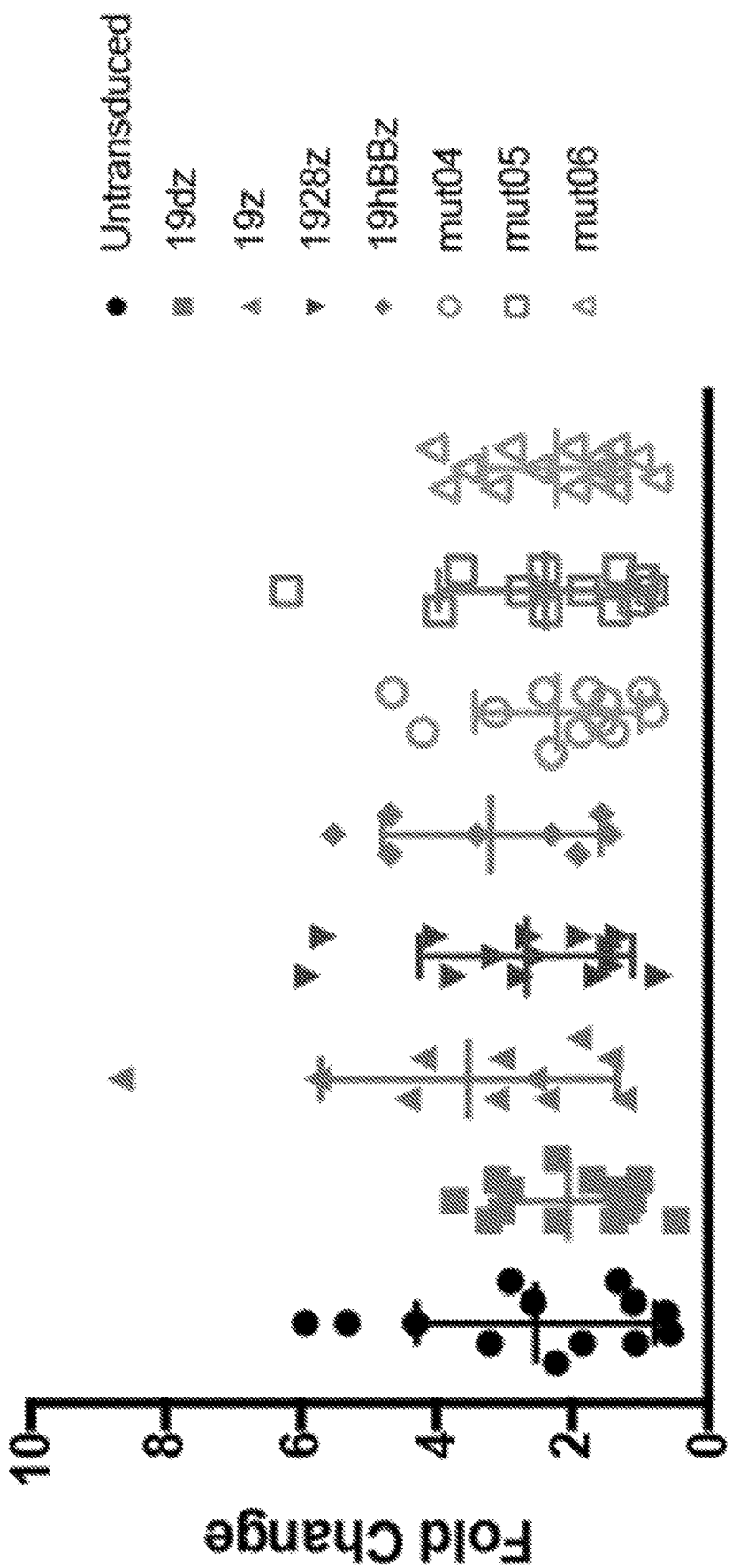
FIG. 5 is a plot showing proliferation of CD28 mutant CAR T cells and non-mutated CAR T cells. CAR T cells were produced from wild type C57BL/6 mice and proliferation was evaluated by fold change from the initial cell number to final cell yield at Day 5.
Figure 6D:
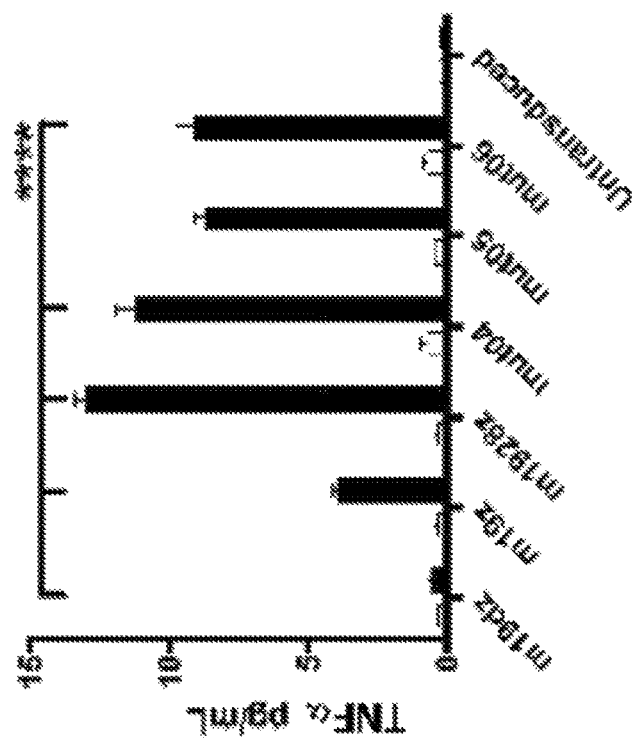
Figure 6C:
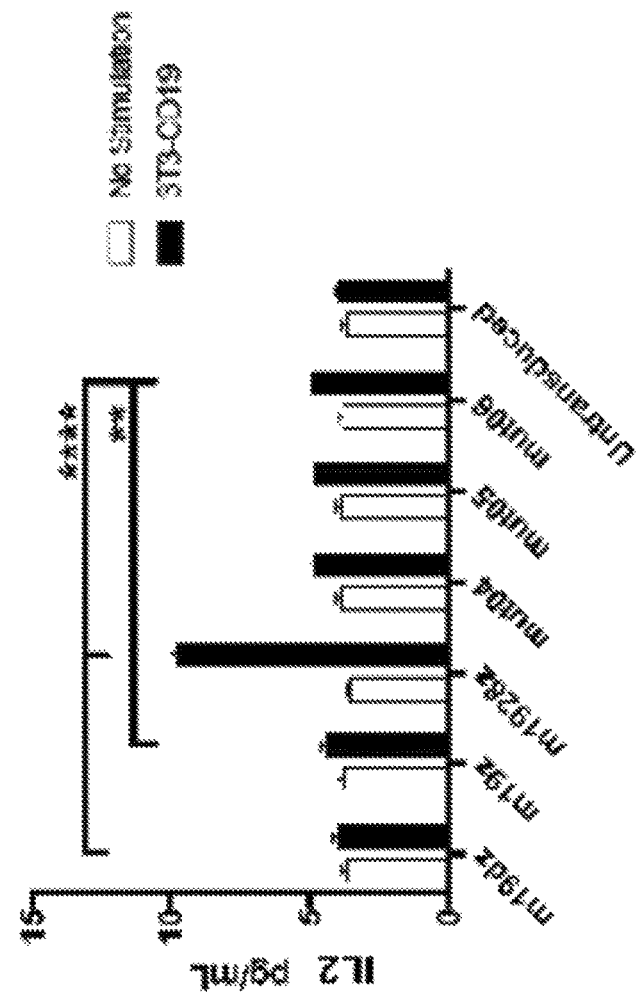
Figure 7A:
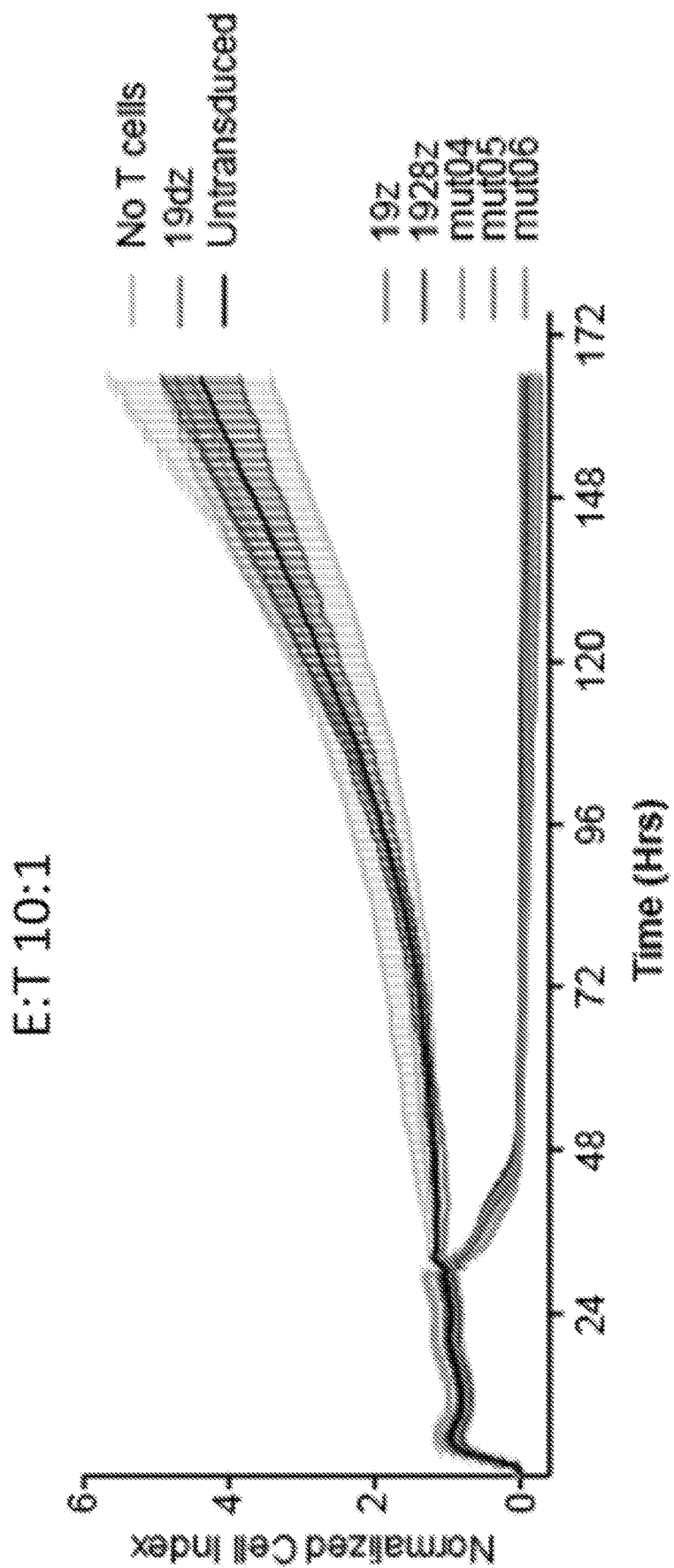
FIGS. 7A and 7B are graphs showing target cell killing by CD28 mutated and non-mutated CAR T cells co-cultured with 3T3-mCD19 target cells at either a 10:1 or 1:6 ratio. Target cell killing was monitored by RTCA.
Figure 7B:
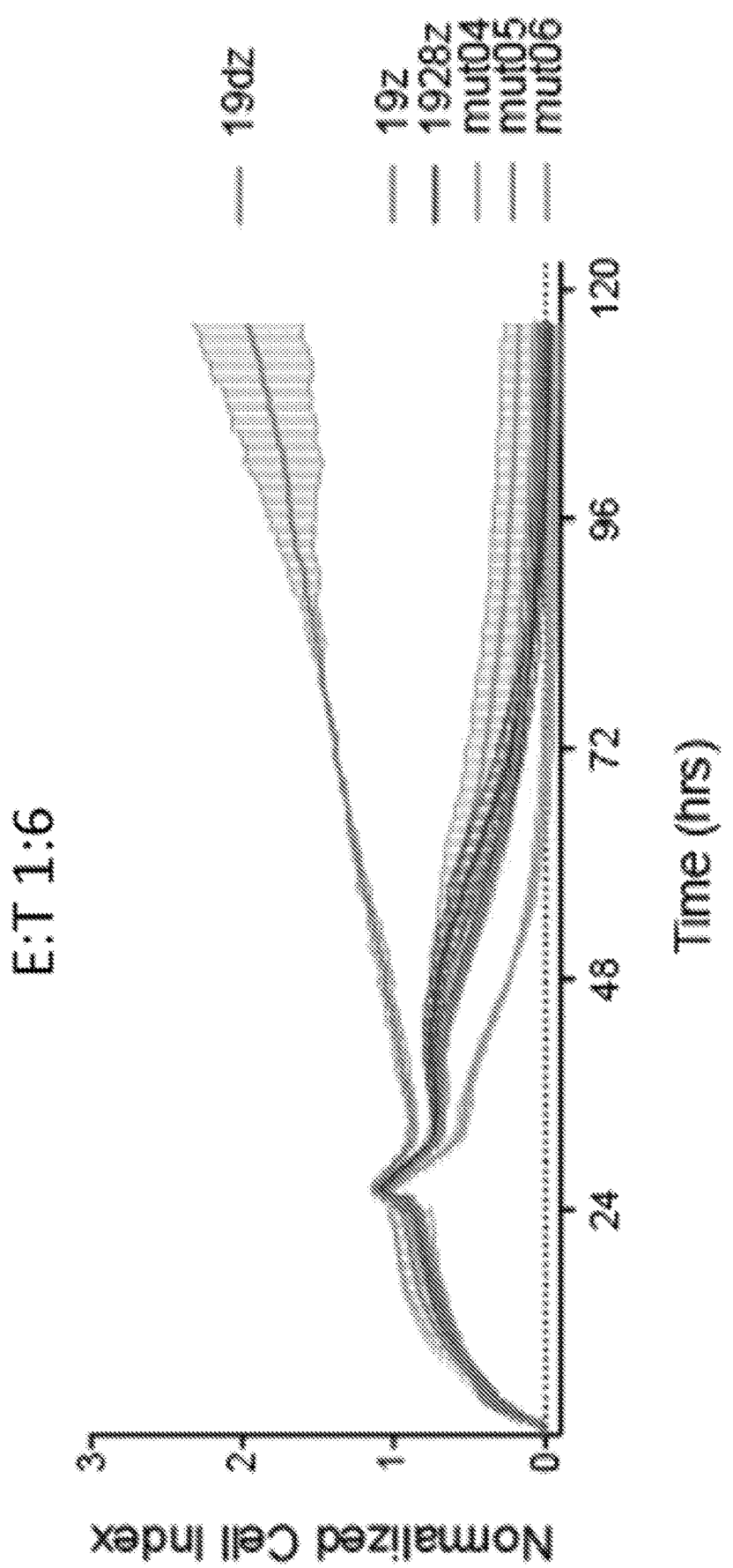
Figure 8B:
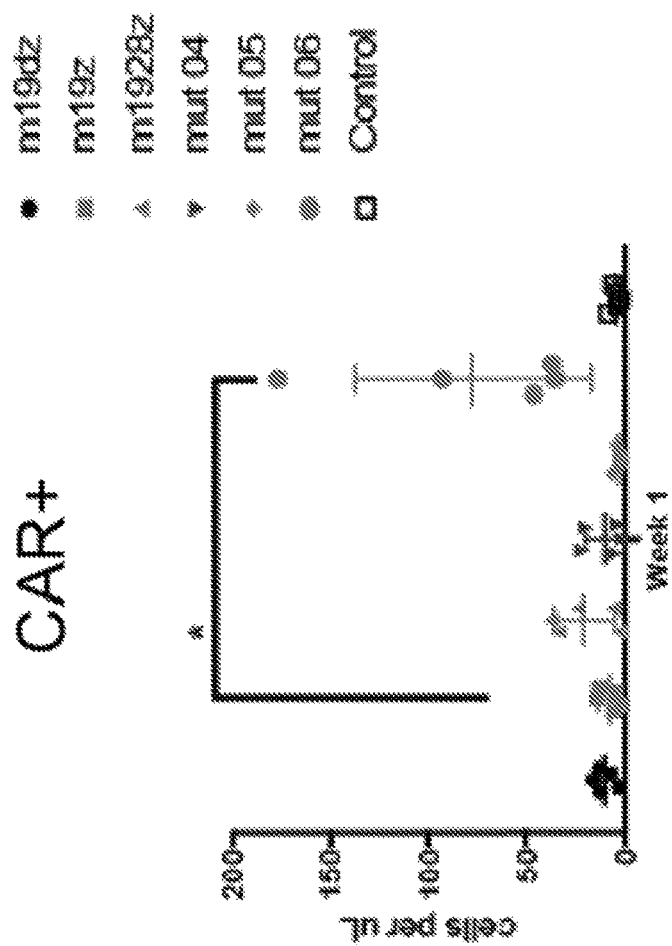
FIGS. 8A to 8H are plots showing B cell killing (FIGS. 8A, 8C, 8E, 8G) and CAR T cell counts (FIGS. 8B, 8D, 8F, 8H) in vivo. 1×10$^6$ CAR T cells (CD3+ CAR+) were i.v. injected into cytoxan (300 mg/kg) pretreated wild type C57BL/6 mice. At weeks 1 (FIGS. 8A, 8B), 2 (FIGS. 8C, 8D), 4 (FIGS. 8E, 8F), and 6 (FIGS. 8G, 8H) mice were bled and B cell and CAR T cell counts were analyzed by flow cytometry.
Figure 8A:
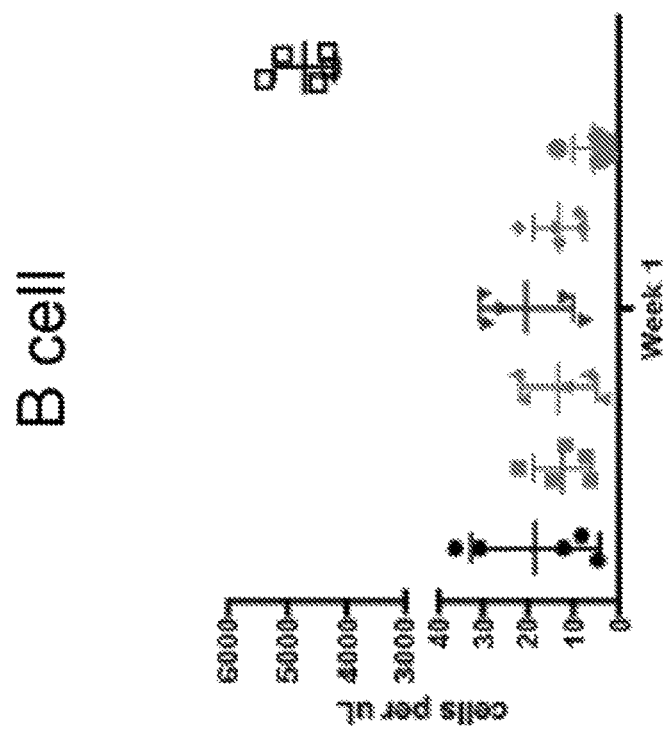
Figure 8D:
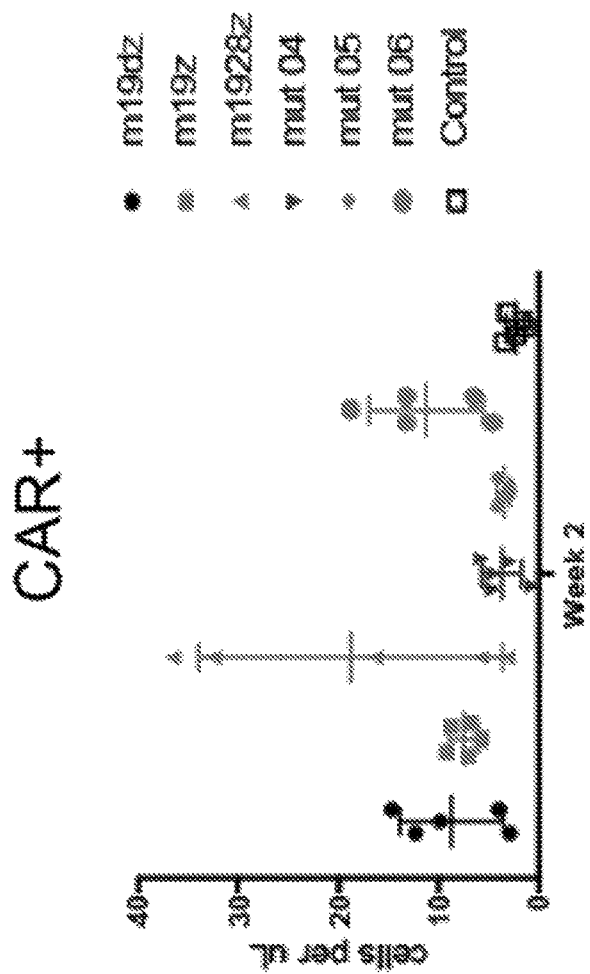
Figure 8C:
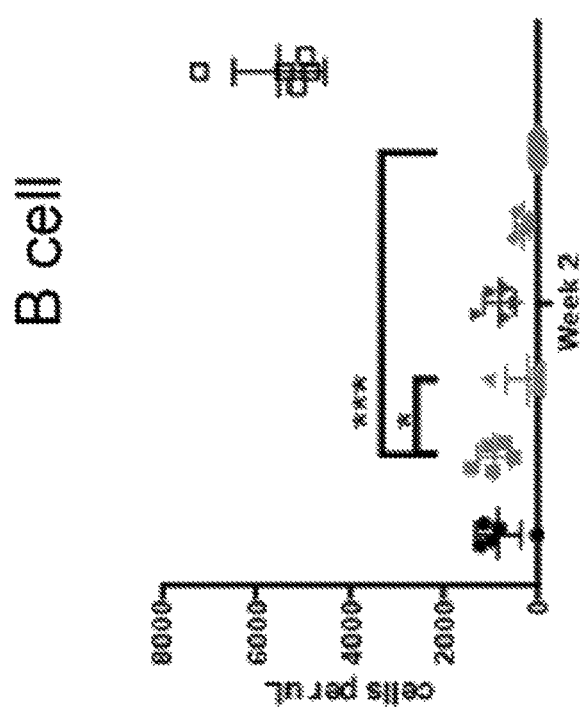
Figure 8F:
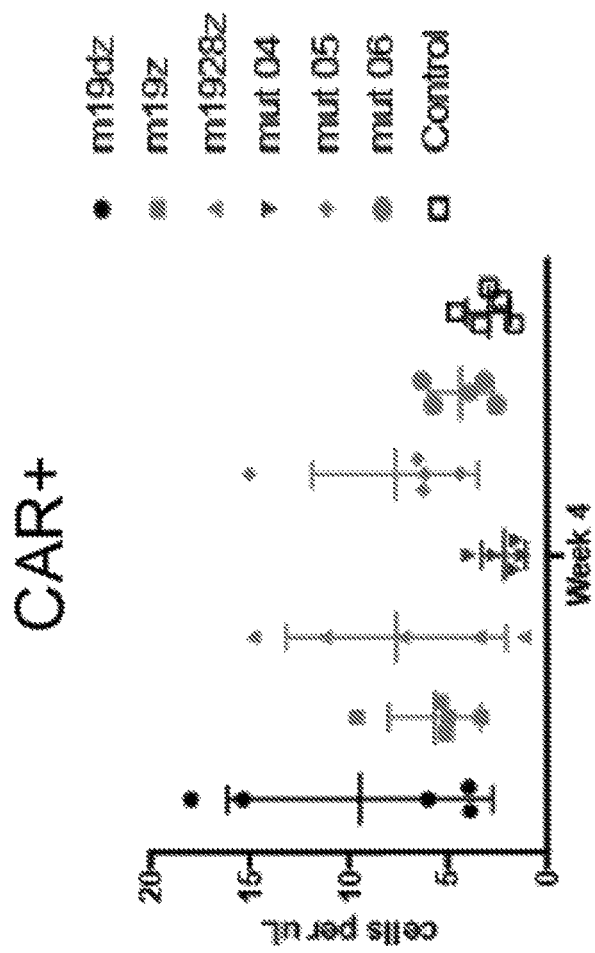
Figure 8E:
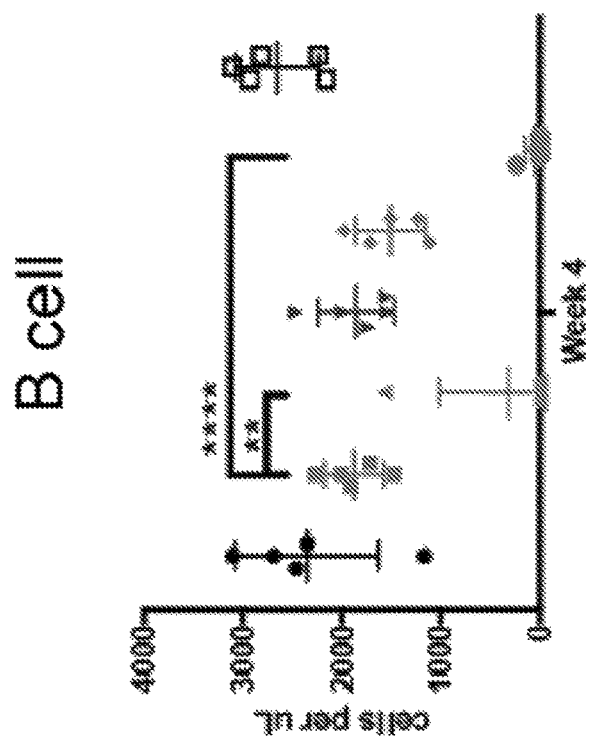
Figure 8H:
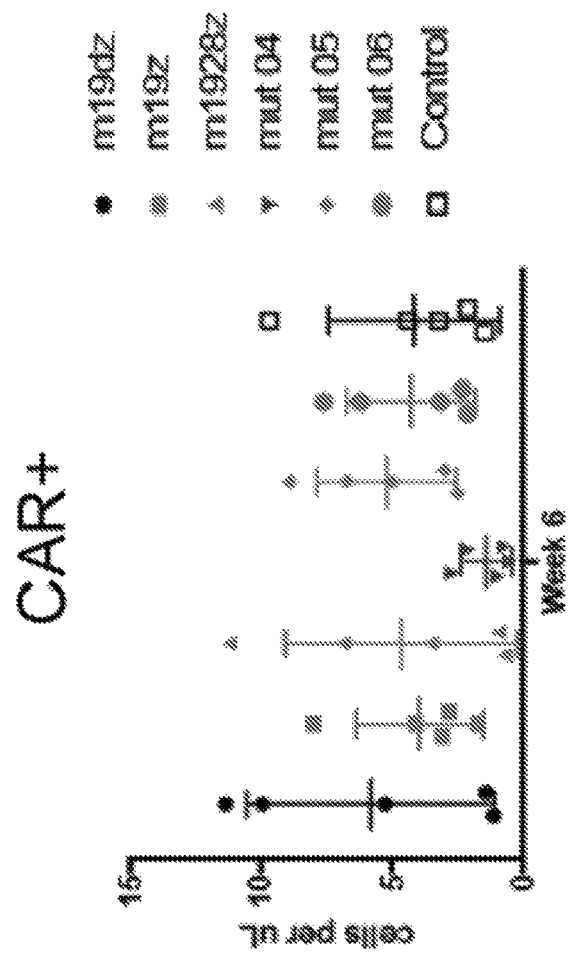
Figure 8G:
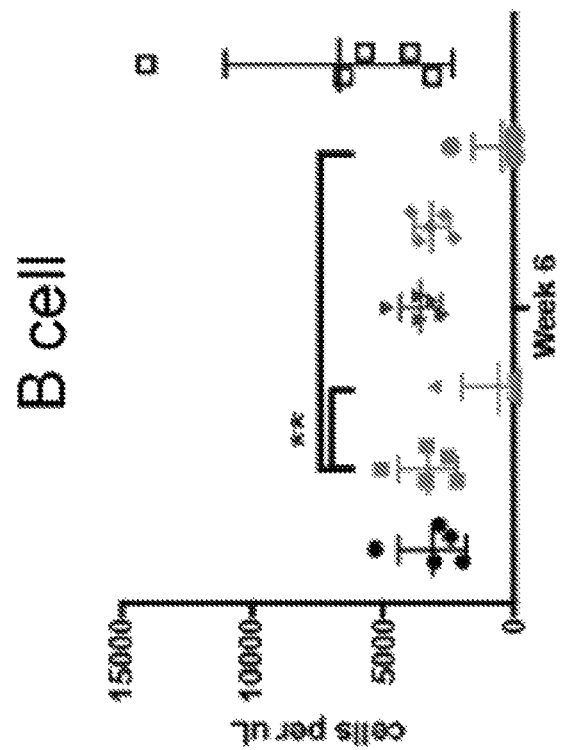
Figure 9D:
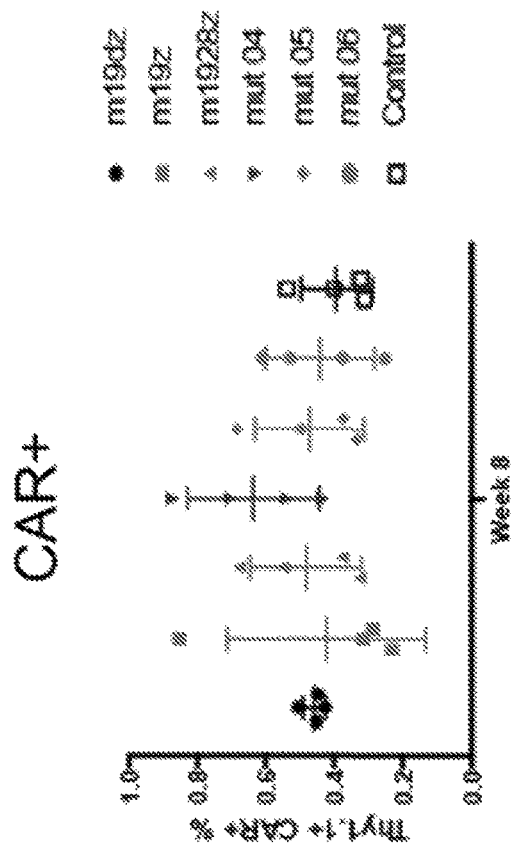
Figure 9C:
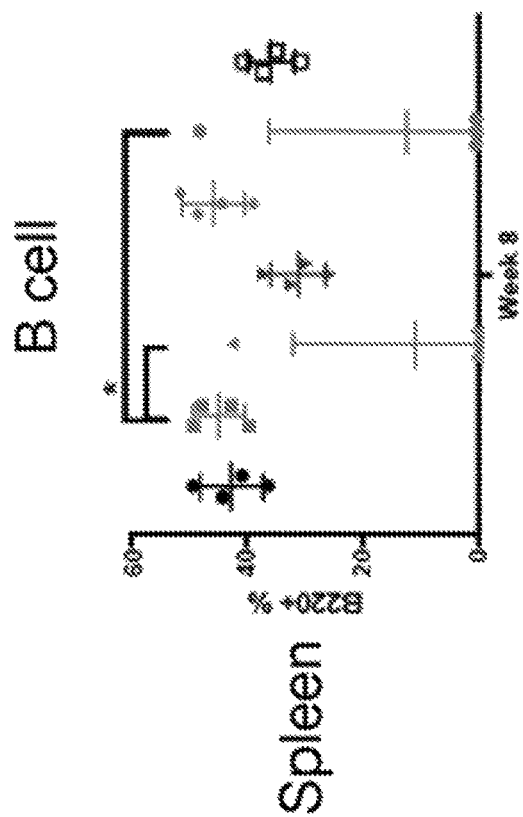
Figure 10:
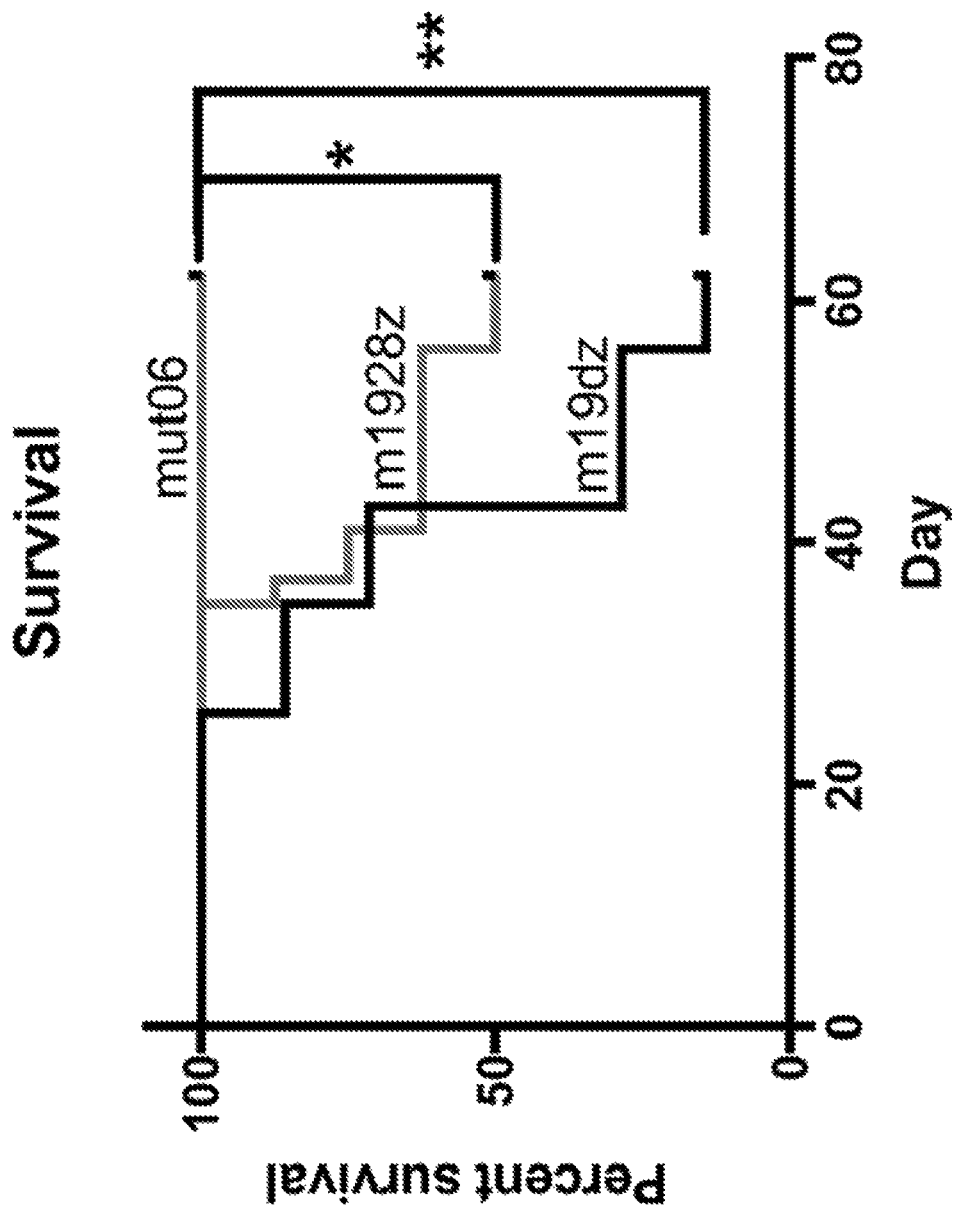
FIG. 10 is a graph showing survival of mice with Eu-ALL tumor after treatment with CAR T cells. Six days after injection with Eu-ALL cells wild type C57BL/6 mice were i.p. injected with cytoxan (300 mg/kg) followed 1 day later with an i.v. injection of 3×10$^5$ CAR T cells.
Figure 11A:
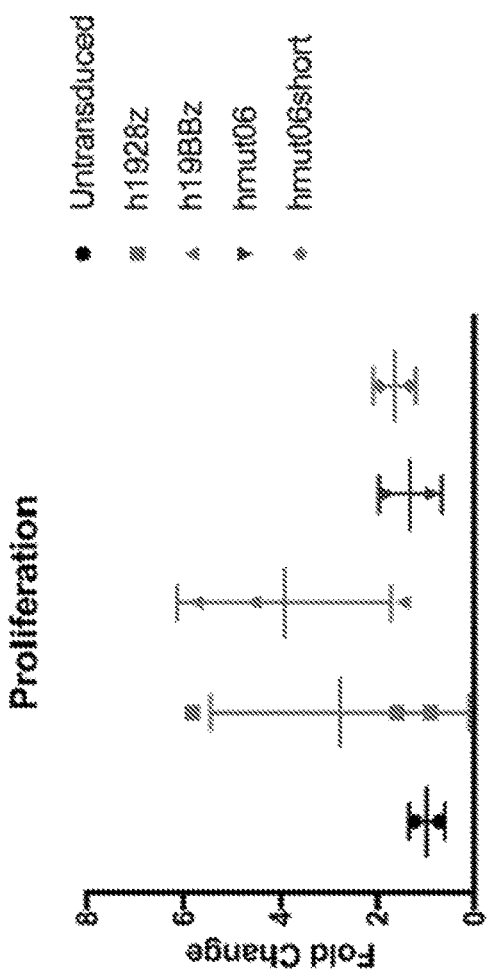
FIGS. 11A and 11B are plots showing proliferation (FIG. 11A) and viability (FIG. 11B) of CD28 mutated and non-mutated CAR T cells. CAR T cells were produced from normal donor PBMCs and cell viability was measured by trypan blue staining on an automated cell counter (BIO-RAD). Proliferation was evaluated by fold change from the initial cell number to final cell yield at Day 5.
Figure 11B:
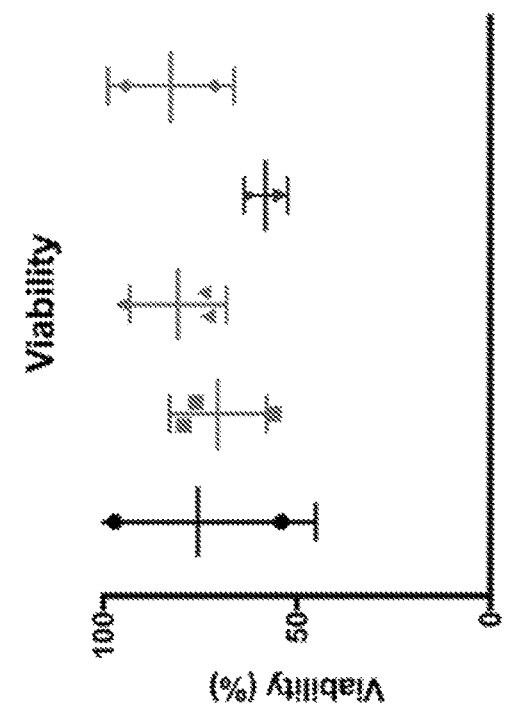
Figure 12:
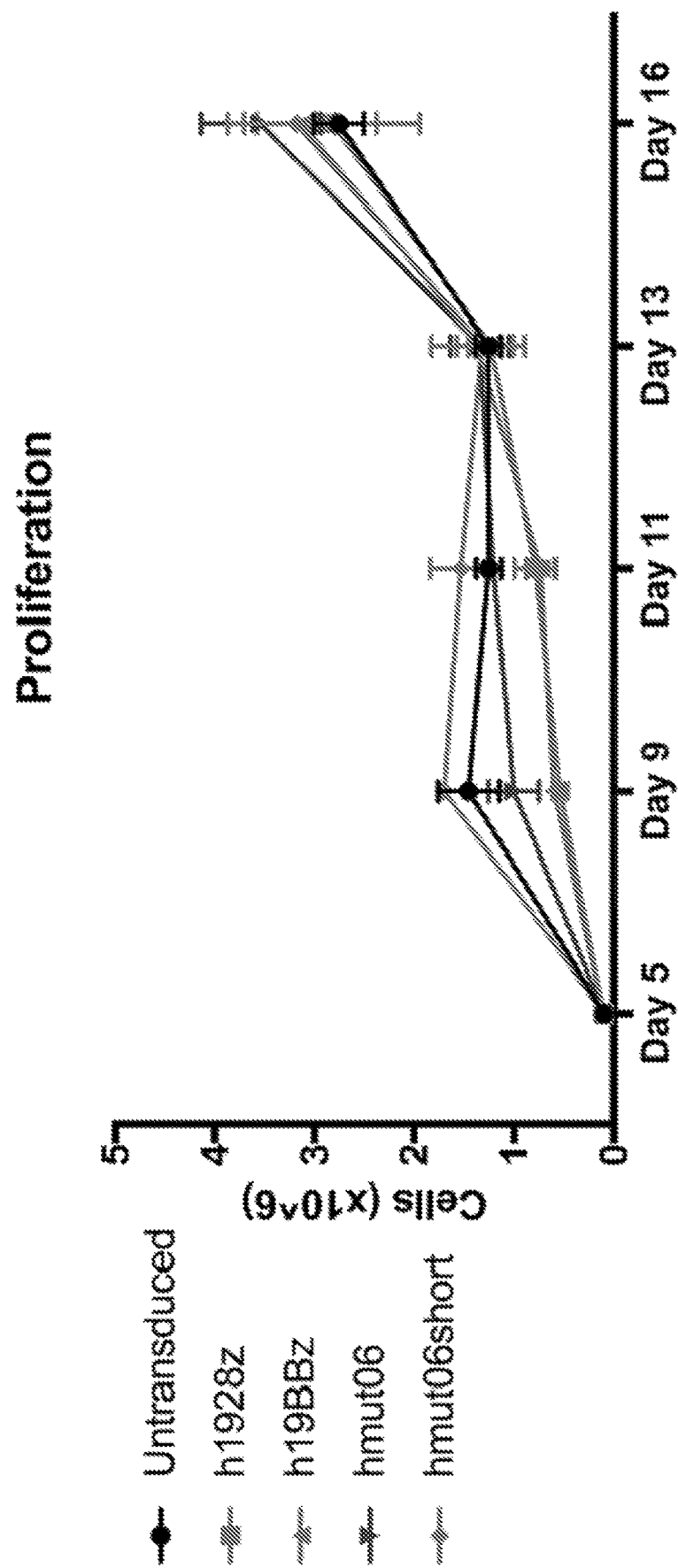
FIG. 12 is a graph showing human CAR T cells proliferation in vitro. 1×10$^5$ human CAR T cells were co-cultured with 3T3-hCD19 cells at a ratio of 10:1 on Day 5 and cell numbers were measured for 10 days.
Figure 13:
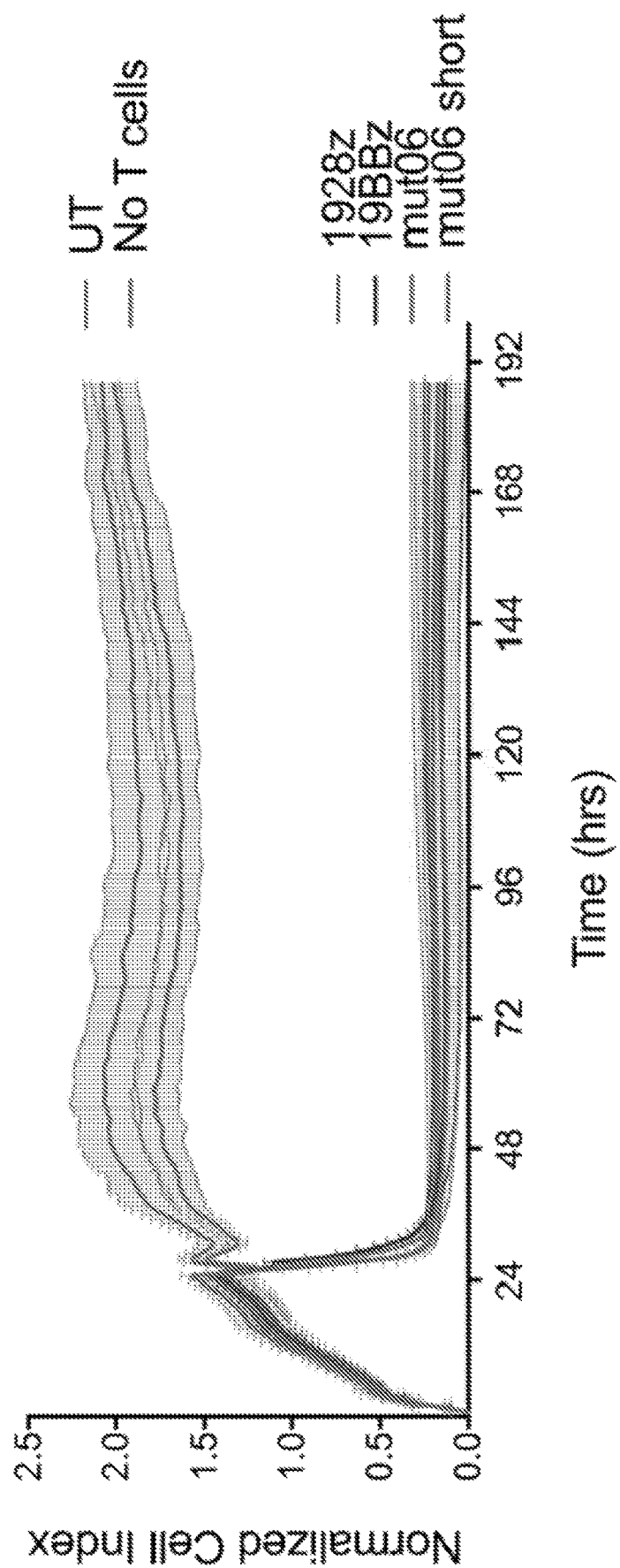
FIG. 13 is a graph showing human mut06 CAR T cells kill as well as non-mutated CAR T cells. CAR T cells were co-cultured with 3T3-hCD19 target cells at a 5:1 ratio. Target cell killing was monitored by RTCA.

To further evaluate the in vitro and in vivo function of CD28 mutated CAR T cells mouse T cells were modified with the CARs and their impact on viability (FIG. 4) and proliferation (FIG. 5) was determined. Secreted cytokine production was also characterized by creating CAR T cells from normal wild-type mice and incubating with 3T3-mCD19 overnight and then secreted cytokine levels were measured. Mut06 CAR T cells produce significantly less cytokines compared to non-mutated 1928z but significantly more cytokines compared to the first generation CAR (FIGS. 6A to 6D). Target cytotoxicity was also characterized by creating CAR T cells from normal wild-type mice and incubating with 3T3-mCD19 and measuring target killing by RTCA over 1 week. CD28 mutant CAR T cells kill as well as non-mutated CAR T cells while at low E:T ratios mut06 killing is superior (FIGS. 7A and 7B). 1×10$^6$ CAR T cells (CD3+ CAR+) were i.v. injected into cytoxan (300 mg/kg) pretreated wild type C57BL/6 mice and then monitored for B cell killing and CAR T cell persistence by serial flow cytometry of blood. At weeks 1 (FIGS. 8A, 8B), 2 (FIGS. 8C, 8D), 4 (FIGS. 8E, 8F), and 6 (FIGS. 8G, 8H) mice Mut06 and 1928z CAR T cells show similar B cell killing and CAR T cell counts in vivo (FIGS. 8A to 8H, 9A to 9D). In vivo killing of leukemia by various CD19-targeted CAR T cells was also compared. Six days after injection with Eu-ALL cells wild type C57BL/6 mice were i.p. injected with cytoxan (300 mg/kg) followed 1 day later with an i.v. injection of $3 \times 10^5$ CAR T cells. Mice with Eu-ALL tumor have significantly longer survival when given mut06 CAR T cells compared to 1928z CRA T cells (FIG. 10). These observation were also extended to human CD28 mutated, human CD19-targeted CAR T cells. Using T cells acquired from healthy donors and modified with human CD19-targeted CAR T cells constructs viability, proliferation, and cytotoxicity were evaluated. Viability and proliferation of CD28 mutated human CAR T cells is similar to non-mutated CAR T cells at the end of production when assayed by trypan blue cell counting (FIGS. 11A and 11B). Also, all human CAR T cells showed similar proliferation in vitro after stimulation with 3T3 cells that express human CD19 (FIG. 12). Compared to non-mutated CAR T cells, human mut06 CAR T cells kill 3T3-human CD19 cells similarly when by measured by RTCA (FIG. 13).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A chimeric antigen receptor (CAR) polypeptide, comprising a co-stimulatory signaling region, wherein the co-stimulatory signaling region comprises a mutated form of a cytoplasmic domain of CD28 having at least one null mutation in a YMNM (SEQ ID NO:1) subdomain, and at least one null mutation in a PRRP (SEQ ID NO:2) subdomain but not having a null mutation in a PYAP (SEQ ID NO:3) subdomain.

2. An isolated nucleic acid sequence encoding the recombinant polypeptide of claim 1.

3. A vector comprising the isolated nucleic acid sequence of claim 2.

4. A cell comprising the vector of claim 3.

5. The cell of claim 4, wherein the cell is selected from the group consisting of an αβT cell, γδT cell, a Natural Killer (NK) cells, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, a regulatory T cell, or any combination thereof.

6. The cell of claim 5, wherein the cell exhibits an anti-tumor immunity when the antigen binding domain of the CAR binds to TAA.

7. A method of providing an anti-tumor immunity in a subject with a TAA-expressing cancer, the method comprising administering to the subject an effective amount of an immune effector cell genetically modified to express the CAR polypeptide of claim 1, thereby providing an anti-tumor immunity in the mammal.

8. The method of claim 7, wherein the immune effector cell is selected from the group consisting of a T cell, a Natural Killer (NK) cell, a cytotoxic T lymphocyte (CTL), and a regulatory T cell.

9. The method of claim 7, further comprising administering to the subject a checkpoint inhibitor.

10. The method of claim 9, wherein the checkpoint inhibitor comprises an anti-PD-1 antibody, anti-PD-L1 antibody, anti-CTLA-4 antibody, or a combination thereof.

* * * * *